(12) United States Patent
Faries, Jr. et al.

(10) Patent No.: US 6,660,974 B2
(45) Date of Patent: Dec. 9, 2003

(54) WARMING SYSTEM AND METHOD FOR HEATING VARIOUS ITEMS UTILIZED IN SURGICAL PROCEDURES

(75) Inventors: Durward I. Faries, Jr., Las Vegas, NV (US); Bruce R. Heymann, Vienna, VA (US); Calvin Blankenship, Frostburg, MD (US); David Hendrix, Ashburn, VA (US)

(73) Assignee: Medical Solutions, Inc., Chantilly, VA (US)

( * ) Notice: Subject to any disclaimer, the term of this patent is extended or adjusted under 35 U.S.C. 154(b) by 0 days.

(21) Appl. No.: 10/127,675

(22) Filed: Apr. 23, 2002

(65) Prior Publication Data
US 2002/0158058 A1 Oct. 31, 2002

Related U.S. Application Data

(63) Continuation-in-part of application No. 09/810,418, filed on Mar. 19, 2001, now Pat. No. 6,376,805, which is a continuation of application No. 09/413,532, filed on Oct. 6, 1999, now Pat. No. 6,294,762, which is a continuation-in-part of application No. PCT/US98/06951, filed on Apr. 7, 1998.
(60) Provisional application No. 60/042,737, filed on Apr. 7, 1997.

(51) Int. Cl.[7] .......................... A61B 19/00; A61B 19/02; A61F 7/00; F27D 7/00; F27D 7/104
(52) U.S. Cl. ..................... 219/400; 219/428; 219/518; 206/370; 604/114; 312/236
(58) Field of Search ................................ 219/385, 386, 219/392, 400, 412, 414, 428, 394, 492, 493, 518; 604/114, 291; 312/209, 236; 222/146.5; 206/363, 370

(56) References Cited

U.S. PATENT DOCUMENTS

| | | |
|---|---|---|
| 1,659,719 A | 2/1928 | Blake |
| 2,175,099 A | 10/1939 | Abbott |
| 2,214,215 A | 9/1940 | Watermann et al. |
| 2,576,874 A | 11/1951 | Acton |
| 2,713,112 A | 7/1955 | Mills et al. |
| 2,741,099 A | 4/1956 | Beane |
| 2,841,132 A | 7/1958 | Philipp |
| 2,885,526 A | 5/1959 | Paulding |
| 2,994,760 A | 8/1961 | Pecoraro et al. |
| 3,051,582 A | 8/1962 | Muckler et al. |
| 3,193,339 A | 7/1965 | Cooper |

(List continued on next page.)

FOREIGN PATENT DOCUMENTS

| | | |
|---|---|---|
| DE | 37 42 927 | 7/1989 |
| DE | 197 52 578 | 6/1999 |

OTHER PUBLICATIONS

Cahill, *New Name, New Helmsman*, JEM, Aug. 1996.
CBi Healthcare Systems, Inc. *Controlled Temperature Cabinet System*, JEMS, Mar. 1997.

(List continued on next page.)

*Primary Examiner*—Joseph Pelham

(57) ABSTRACT

A surgical warming system includes at least one and generally two or more compartments, whereby each compartment is separately heatable and controllable over its own range of temperatures. The compartments may be implemented as separate warmer units in stacked relation. Alternatively, the compartments may be constructed into a single cabinet structure. The heat within each compartment is provided by forcing air through a heating chamber and into the compartment whereby the forced air is recycled and mixed with make-up air. Each individually controllable compartment enables an operator to simultaneously maintain the individual compartments of the same warming system at different desired temperatures. In addition, the warming system further includes for each compartment a display and a tray or drawer with individual receptacles and corresponding monitoring assemblies in order to indicate the temperature and residence time of each item heated within that compartment.

69 Claims, 8 Drawing Sheets

U.S. PATENT DOCUMENTS

| | | | |
|---|---|---|---|
| 3,241,603 A | 3/1966 | Nagata | |
| 3,255,812 A | 6/1966 | Bayane et al. | |
| 3,329,202 A | 7/1967 | Birman | |
| 3,353,589 A | 11/1967 | Tope et al. | |
| 3,386,498 A | 6/1968 | Funfstuck | |
| 3,485,245 A | 12/1969 | Lahr et al. | |
| 3,536,132 A | 10/1970 | Pecoraro et al. | |
| 3,590,215 A | 6/1971 | Anderson et al. | |
| 3,612,165 A | 10/1971 | Haynes | |
| 3,713,302 A | 1/1973 | Reviel | |
| 3,777,187 A | 12/1973 | Kohn | |
| 3,801,278 A * | 4/1974 | Wagner et al. | 219/521 |
| 3,826,305 A | 7/1974 | Fishman | |
| 3,858,106 A | 12/1974 | Launius | |
| 3,879,171 A | 4/1975 | Tulis | |
| 4,024,377 A | 5/1977 | Henke | |
| 4,084,080 A | 4/1978 | McMahan | |
| 4,090,514 A | 5/1978 | Hinck et al. | |
| 4,189,995 A | 2/1980 | Löhr et al. | |
| 4,233,495 A | 11/1980 | Scoville et al. | |
| 4,309,592 A | 1/1982 | Le Boeuf | |
| 4,318,276 A | 3/1982 | Sato et al. | |
| 4,328,676 A | 5/1982 | Reed | |
| 4,331,859 A | 5/1982 | Thomas et al. | |
| 4,364,234 A | 12/1982 | Reed | |
| 4,407,133 A | 10/1983 | Edmonson | |
| 4,419,568 A | 12/1983 | Van Overloop | |
| 4,455,478 A | 6/1984 | Guibert | |
| 4,464,563 A | 8/1984 | Jewett | |
| 4,495,402 A | 1/1985 | Burdick et al. | |
| 4,523,078 A | 6/1985 | Lehmann | |
| 4,605,840 A | 8/1986 | Koopman | |
| 4,657,004 A | 4/1987 | Coffey | |
| 4,678,460 A | 7/1987 | Rosner | |
| 4,680,445 A | 7/1987 | Ogawa | |
| 4,707,587 A | 11/1987 | Greenblatt | |
| 4,726,193 A | 2/1988 | Burke et al. | |
| 4,745,248 A | 5/1988 | Hayes | |
| 4,801,777 A | 1/1989 | Auerbach | |
| 4,814,570 A * | 3/1989 | Takizaki | 219/518 |
| 4,823,554 A | 4/1989 | Trachtenberg et al. | |
| 4,874,033 A | 10/1989 | Chatelain et al. | |
| 4,894,207 A | 1/1990 | Archer et al. | |
| 4,906,816 A | 3/1990 | van Leerdam | |
| 4,910,386 A | 3/1990 | Johnson | |
| 4,923,681 A * | 5/1990 | Cox et al. | 219/492 |
| 4,934,336 A | 6/1990 | White | |
| 4,935,604 A | 6/1990 | Allen et al. | |
| 4,961,320 A | 10/1990 | Gutmann | |
| 5,061,241 A | 10/1991 | Stephens, Jr. et al. | |
| 5,061,630 A | 10/1991 | Knopf et al. | |
| 5,081,697 A | 1/1992 | Manella | |
| 5,106,373 A | 4/1992 | Augustine et al. | |
| 5,108,372 A | 4/1992 | Swenson | |
| 5,125,900 A | 6/1992 | Teves | |
| 5,129,033 A | 7/1992 | Ferrara et al. | |
| 5,172,347 A * | 12/1992 | Masuda | 607/154 |
| 5,183,994 A | 2/1993 | Bowles, Sr. et al. | |
| 5,195,976 A | 3/1993 | Swenson | |
| 5,217,064 A | 6/1993 | Kellow et al. | |
| 5,243,833 A | 9/1993 | Coelho et al. | |
| 5,263,929 A | 11/1993 | Falcone et al. | |
| 5,276,310 A | 1/1994 | Schmidt et al. | |
| 5,282,264 A | 1/1994 | Reeves et al. | |
| 5,297,234 A | 3/1994 | Harms et al. | |
| 5,315,830 A | 5/1994 | Doke et al. | |
| 5,333,326 A | 8/1994 | Faries, Jr. et al. | |
| 5,345,923 A | 9/1994 | Luebke et al. | |
| 5,364,385 A | 11/1994 | Harms et al. | |
| 5,381,510 A | 1/1995 | Ford et al. | |
| 5,397,875 A | 3/1995 | Bechtold, Jr. | |
| 5,399,007 A | 3/1995 | Marconet | |
| 5,408,576 A | 4/1995 | Bishop | |
| 5,483,799 A | 1/1996 | Dalto | |
| 5,540,901 A * | 7/1996 | Riley | 206/370 |
| 5,572,873 A | 11/1996 | Lavigne et al. | |
| 5,653,905 A | 8/1997 | McKinney | |
| 5,661,978 A | 9/1997 | Holmes et al. | |
| 5,729,653 A | 3/1998 | Magliochetti et al. | |
| 5,733,263 A | 3/1998 | Wheatman | |
| 5,786,568 A | 7/1998 | McKinney | |
| 5,858,303 A | 1/1999 | Schiffmann et al. | |
| 5,868,195 A * | 2/1999 | Westbrooks, Jr. | 219/386 |
| 5,868,250 A * | 2/1999 | Brackett | 206/363 |
| 5,879,329 A | 3/1999 | Ginsburg | |
| 5,897,207 A | 4/1999 | Hartmann | |
| 5,910,210 A | 6/1999 | Violi et al. | |
| 5,924,289 A | 7/1999 | Bishop, II | |
| 5,961,492 A | 10/1999 | Kriesel et al. | |
| 5,977,520 A | 11/1999 | Madson, Jr. et al. | |
| 5,986,239 A | 11/1999 | Corrigan, III et al. | |
| 5,989,238 A | 11/1999 | Ginsburg | |
| 6,039,926 A * | 3/2000 | Goldman | 219/492 |
| 6,124,572 A | 9/2000 | Spilger et al. | |
| 6,174,300 B1 | 1/2001 | Kriesel et al. | |
| 6,175,099 B1 | 1/2001 | Shei et al. | |
| 6,259,067 B1 | 7/2001 | Faries, Jr. et al. | |
| 6,316,750 B1 * | 11/2001 | Levin | 604/291 |
| 6,384,380 B1 | 5/2002 | Faries, Jr. et al. | |

OTHER PUBLICATIONS

Koolatron, *P–34 Precision Control Theroelectric Cooler/Warmer*, Jan. 1998.

Koolatron, *Canadian company announces the release of a precision control unit*, Aug. 1997.

Anton, 500 miles from nowhere, it'll give you a cold drink or a warm burger . . . , Technology Update, 1993.

Koolatron, 1997 U.S. $ Price List, 1997.

Kellow et al, *Drug Adulteration in Prehospital Emergency Medical Services*, Oct. 1994.

CBi Medical, Inc., *IV Fluid Warmer Model 8362*, 1992.

* cited by examiner

FIG.8

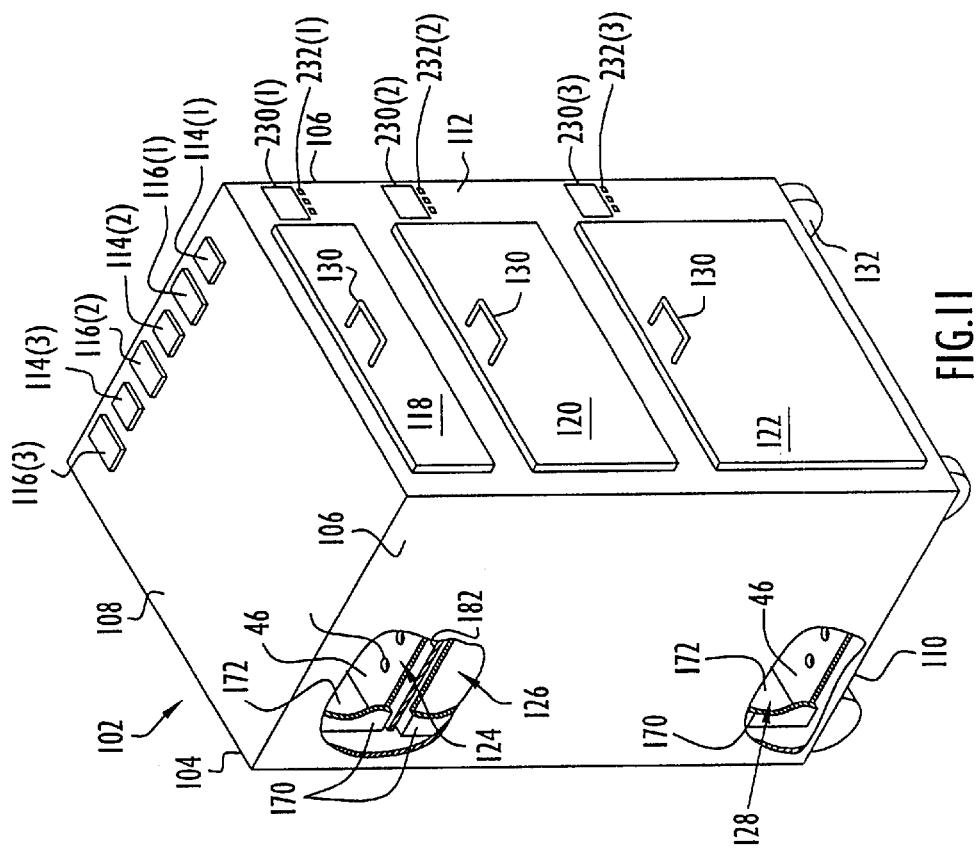
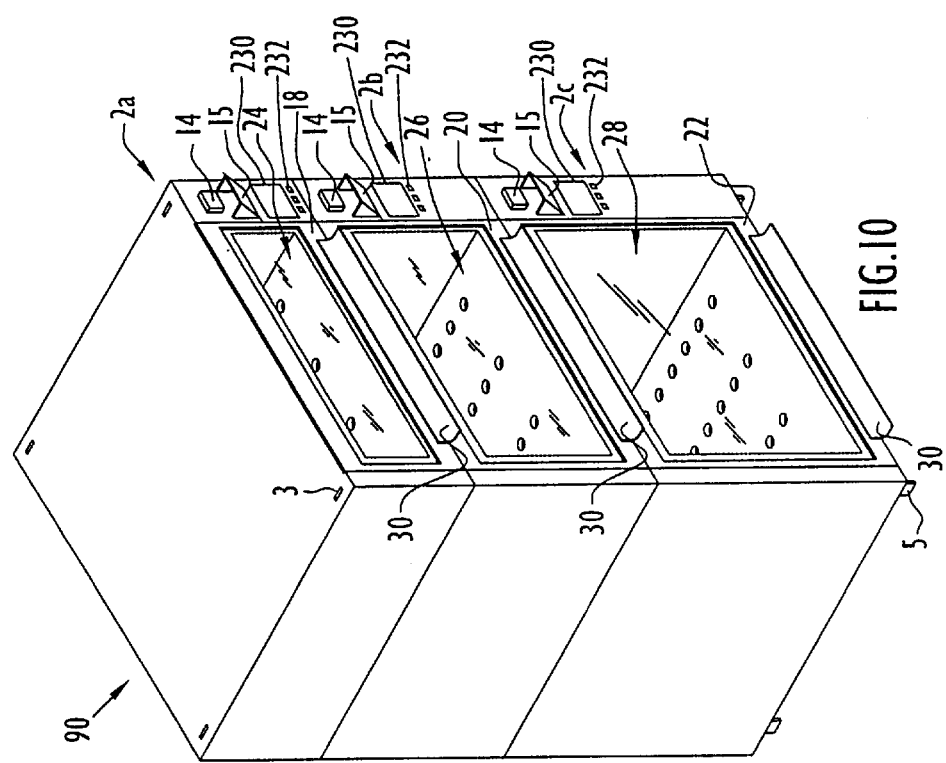

WARMING SYSTEM AND METHOD FOR HEATING VARIOUS ITEMS UTILIZED IN SURGICAL PROCEDURES

CROSS-REFERENCE TO RELATED APPLICATIONS

This application is a continuation-in-part of U.S. patent application Ser. No. 09/810,418, entitled "Warming System and Method for Heating Various Items Utilized in Surgical Procedures" and filed Mar. 19, 2001, now U.S. Pat. No. 6,376,805 which is a continuation of U.S. patent application Ser. No. 09/413,532, entitled "Warming System and Method for Heating Various Items Utilized in Surgical Procedures" and filed Oct. 6, 1999, now U.S. Pat. No. 6,294,762, which is a continuation-in-part of International Application No. PCT/US 98/06951, entitled "Warming System and Method for Heating Various Items Utilized in Surgical Procedures" and filed Apr. 7, 1998, which claims priority from U.S. Provisional Patent Application Serial No. 60/042,737, entitled "Warmer Cabinet for Use in Surgical Procedures" and filed Apr. 7, 1997. The disclosures of the above-mentioned patent and International and U.S. patent applications are incorporated herein by reference in their entireties.

BACKGROUND OF THE INVENTION

1. Technical Field

The present invention pertains to surgical warming systems for heating various items. In particular, the present invention pertains to a warming system and method for heating intravenous (IV) solution contained within bags and/or bottles, surgical instruments, blood and drugs placed within appropriate containers, or other objects for use in surgical procedures.

2. Discussion of Related Art

Generally, various items are required to be heated prior to utilization in a medical procedure to prevent thermal shock and injury to a patient. These items typically include intravenous solution, surgical instruments, bottles and blankets. In order to provide the necessary heated items for use in medical procedures, medical personnel may utilize several types of warming systems to heat items toward their operational temperatures. For example, ovens may be disposed within operating rooms to heat items to desired temperatures. Further, U.S. Pat. No. 4,495,402 (Burdick et al) discloses a warmer for heating wet dressings and other articles disposed within a heating and storage compartment. The articles are arranged within the compartment in stacked relation and disposed on a plate that is supplied with thermal energy from a heater. The plate includes a center aperture whereby a first thermal sensor is disposed in the aperture in contact with a bottommost article. Control circuitry is disposed beneath the plate to control the heater to maintain temperature of the bottommost article at a desired level based on the temperatures sensed by the first thermal sensor and a second thermal sensor responsive to heater temperature.

U.S. Pat. No. 5,408,576 (Bishop) discloses an intravenous fluid warmer having a cabinet structure to accommodate a plurality of intravenous fluid bags. A temperature sensor and pad of heating filaments are disposed within the cabinet structure, whereby the temperature sensor measures the pad temperature and enables automatic temperature regulation of the pad to heat the intravenous fluid bags. The heating filaments are covered by a rubber layer to prevent melting of the bags during heating. A temperature indicator connected to the temperature sensor and disposed on the cabinet structure permits a user to ascertain when a desired temperature is attained, whereby an intravenous fluid bag is removed from the intravenous fluid warmer via an opening defined in a side of the cabinet structure.

The warming systems described above suffer from several disadvantages. In particular, ovens typically do not have a high degree of accuracy or control, thereby enabling use of items having temperatures incompatible with a medical procedure and possibly causing injury to a patient. Further, the Burdick et al and Bishop warmers employ heaters that generally contact a portion of the article being heated, thereby heating the articles in an uneven manner and enabling formation of hot spots. Moreover, the Burdick et al and Bishop warmers generally permit direct contact between an article and a heater, thereby enabling the article to become damaged from excess heat.

In order to overcome the aforementioned problems, some warming systems utilize heated air to heat articles placed within these systems. For example, U.S. Pat. No. 5,282,264 (Reeves et al) discloses an apparatus for thawing and warming solutions or fluids for intravenous administration. The solutions are typically contained within bags and placed within a tray disposed toward the top of an apparatus cabinet. A heating element is disposed within the apparatus cabinet whereby an impeller forces air past the heating element and into an air plenum. The air plenum extends from within the apparatus cabinet and curves over the top of the tray to direct and evenly distribute the heated air over various articles placed in the tray. A temperature sensor measures air temperature to enable a controller to maintain the heated air within a desired temperature range.

U.S. Pat. No. 5,297,234 (Harms et al) discloses an apparatus for rapid thermal processing of transfusion fluid, such as blood or blood components. The apparatus thaws a bag containing frozen blood or blood components by directing a flow of air across a heating coil. Temperature sensors measure the temperatures of the air and blood, whereby a control system monitors the sensed air temperature to maintain air temperature at a particular level, and terminates thawing in response to a bag temperature of 30° C. The apparatus further enables rapid freezing of blood by directing air across a cooling coil and upon a bag containing blood to freeze that blood. The control system monitors sensed blood temperature via the temperature sensor, and terminates freezing in response to a bag or blood temperature of −30° C. The control system further facilitates display of the sensed bag temperatures on an operator display.

The warming systems described above utilizing heated air to warm items suffer from several disadvantages. In particular, the warming systems heat items simultaneously to only a single desired temperature, thereby being incompatible for applications requiring various items to be heated to different temperature ranges. Further, the warming systems control item temperature based on temperature of flowing air measured within a compartment separate from the items, thereby providing less accurate temperature control of the item storage compartment and for maintaining items at a desired temperature. Moreover, the warming systems have fixed storage capacities and are limited to a certain quantity or size of items, thereby being incompatible with items having dimensions beyond those of the respective system storage capacities, and/or requiring use of additional systems or heating cycles to accommodate additional items. Conversely, the warming systems may utilize excess resources when used for quantities of items substantially less than their storage capacities. In addition, the above-described warming systems do not provide an indication of the amount of time items reside within the systems. Thus, medical personnel may unknowingly administer to patients solutions and/or medication that are unusable and/or have reduced potency due to prolonged exposure to heat, thereby risking serious injury to the patients.

OBJECTS AND SUMMARY OF THE INVENTION

Accordingly, it is an object of the present invention to simultaneously maintain various items at different desired temperatures for use in medical procedures.

It is another object of the present invention to simultaneously maintain various items at different desired temperatures for use in medical procedures via a warming system constructed of individually controlled and various sized warmer units, whereby each warmer unit is maintained at an associated desired temperature.

Yet another object of the present invention to simultaneously maintain various items at different desired temperatures for use in medical procedures via a warming system including a single cabinet structure having multiple compartments, whereby each compartment is maintained at an associated desired temperature.

Still another object of the present invention is to simultaneously maintain various items at desired temperatures via a warming system having a selectively adjustable storage capacity to accommodate varying quantities or sizes of items for different applications.

A further object of the present invention is to indicate to medical personnel the temperature and residence times of each item being heated within a warming system.

The aforesaid objects may be achieved individually and/or in combination, and it is not intended that the present invention be construed as requiring two or more of the objects to be combined unless expressly required by the claims attached hereto.

According to the present invention, a surgical warming system provides a manner in which to heat various medical items, primarily medical solutions generally contained within different sized bags and/or bottles, independently and simultaneously to enable the items to be immediately utilized for a particular medical application. The term "medical solutions" used herein refers to intravenous solutions, blood or other solutions that are administered intravenously to a patient. Specifically, the surgical warming system includes various compartments, at least one and generally two or more compartments, whereby each compartment is separately heatable and controllable over its own range of temperatures, typically in the approximate range of 86° F.–104° F. The compartments may be modular in the sense that the compartments may be implemented as separate warmer units that are stacked one atop the other. Alternatively, the multiple compartments may be constructed into a single cabinet structure whereby the compartments have varying dimensions, preferably to receive different sized intravenous bags and/or bottles. The heat within each compartment is provided by forcing air through a heating chamber and into the compartment whereby the forced air is recycled and mixed with make-up (e.g., outside) air to maximize control of air temperature. Each individually controllable compartment includes a corresponding heating unit and controller that enables an operator to simultaneously maintain the individual compartments of the same warming system at different desired temperatures in order to heat items or groups of items contained within the respective compartments to those different temperatures. In addition, the warming system further includes for each compartment a display and a tray or drawer with individual receptacles and corresponding monitoring assemblies in order to monitor medical items placed within the drawer and indicate the temperature and residence time of each item heated within that compartment.

The above and still further objects, features and advantages of the present invention will become apparent upon consideration of the following detailed description of specific embodiments thereof, particularly when taken in conjunction with the accompanying drawings wherein like reference numerals in the various figures are utilized to designate like components.

BRIEF DESCRIPTION OF THE DRAWINGS

FIG. 6b is a top view in plan of the tray or drawer of FIG. 6a.

FIG. 6c is a front view in elevation and partial section of the tray or drawer of FIG. 6a.

FIG. 6d is a side view in elevation of the tray or drawer of FIG. 6a.

FIG. 7 is a view in perspective of an exemplary monitoring assembly utilized with the tray or drawer of FIG. 6a.

FIG. 8 is a schematic illustration of an exemplary display screen for the warmer unit of FIG. 1 according to the present invention.

FIG. 10 is a view in perspective of a warming system including a plurality of warmer units of the type of FIG. 1 to simultaneously maintain various objects at different desired temperatures according to the present invention.

FIG. 11 is a view in perspective of an exemplary warming system having multiple compartments constructed into a single cabinet structure according to the present invention.

DETAILED DESCRIPTION OF THE PREFERRED EMBODIMENTS

Figure 1:
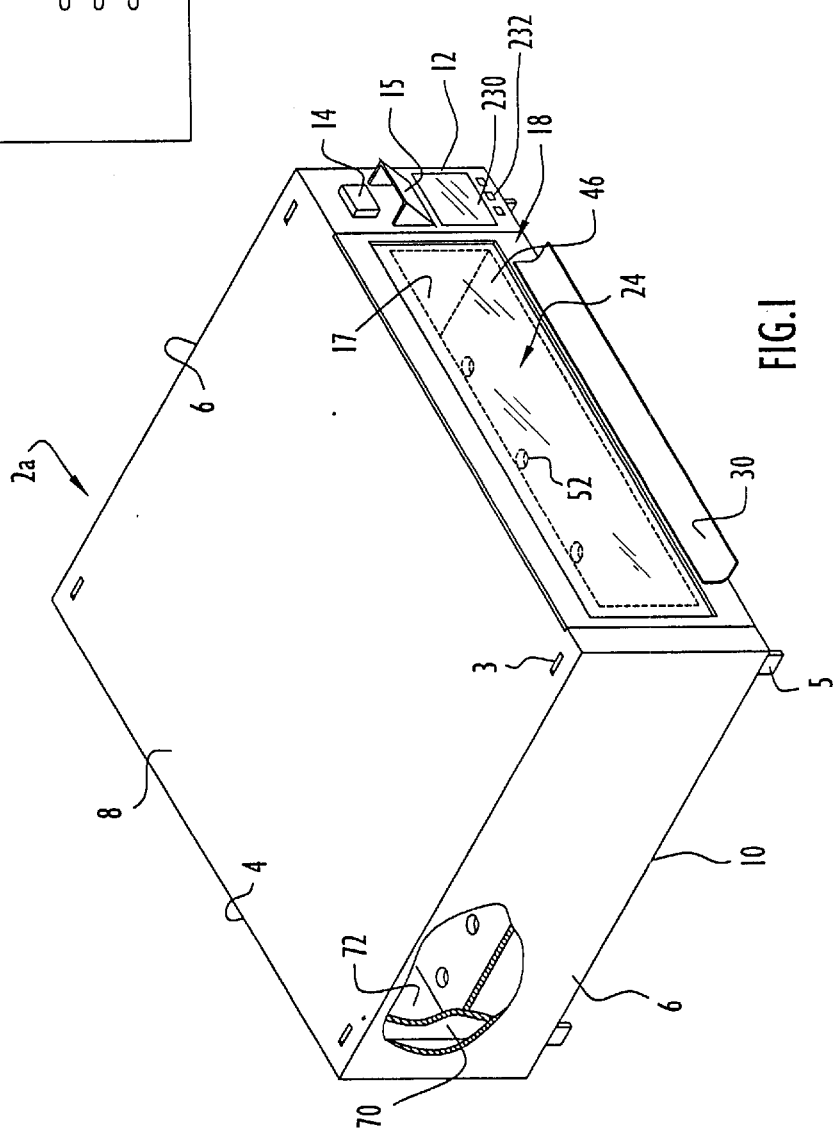
FIG. 1 is a view in perspective of an exemplary modular warmer unit according to the present invention.

An exemplary surgical warmer unit 2a of the present invention is illustrated in FIG. 1. Specifically, warmer unit 2a includes a rear panel 4, two substantially similar side panels 6, a top panel 8, a bottom panel 10 and a front panel 12. The top, side, front, rear and bottom panels are each substantially rectangular and define a cabinet interior wherein various medical or other items maybe heated. The terms "top", "bottom", "side", "left", "right", "front", "rear", "upper", "lower", "length", "width", "height", "depth", "horizontal" and "vertical" are utilized herein merely to indicate points of reference and do not limit the present invention to any specific orientation or configuration. Warmer unit 2a is similar to the warmer unit described in the aforementioned U.S. Pat. No. 6,294,762 and includes a compartment 24 that is controlled by a corresponding process controller 16 (FIG. 9) to maintain a desired heating (i.e., temperature) range, whereby the compartment maybe set and maintained at a desired or set point temperature as described below. A series of substantially rectangular slots 3 are disposed toward the corners of top panel 8, while a plurality of substantially rectangular feet or tabs 5 extend from the proximity of the corners of bottom panel 10. Slots 3 include dimensions slightly larger than feet 5 to enable feet 5 of warmer unit 2a to be inserted within slots 3 of a warmer unit disposed below warmer unit 2a. This enables warmer units to be arranged in stacked relation to form warming systems or cabinets having a plurality of warmer units (e.g., FIG. 10). The warmer unit slots and feet may be of any quantity, shape or size, and may be disposed on the warmer unit in any fashion.

Figure 9:
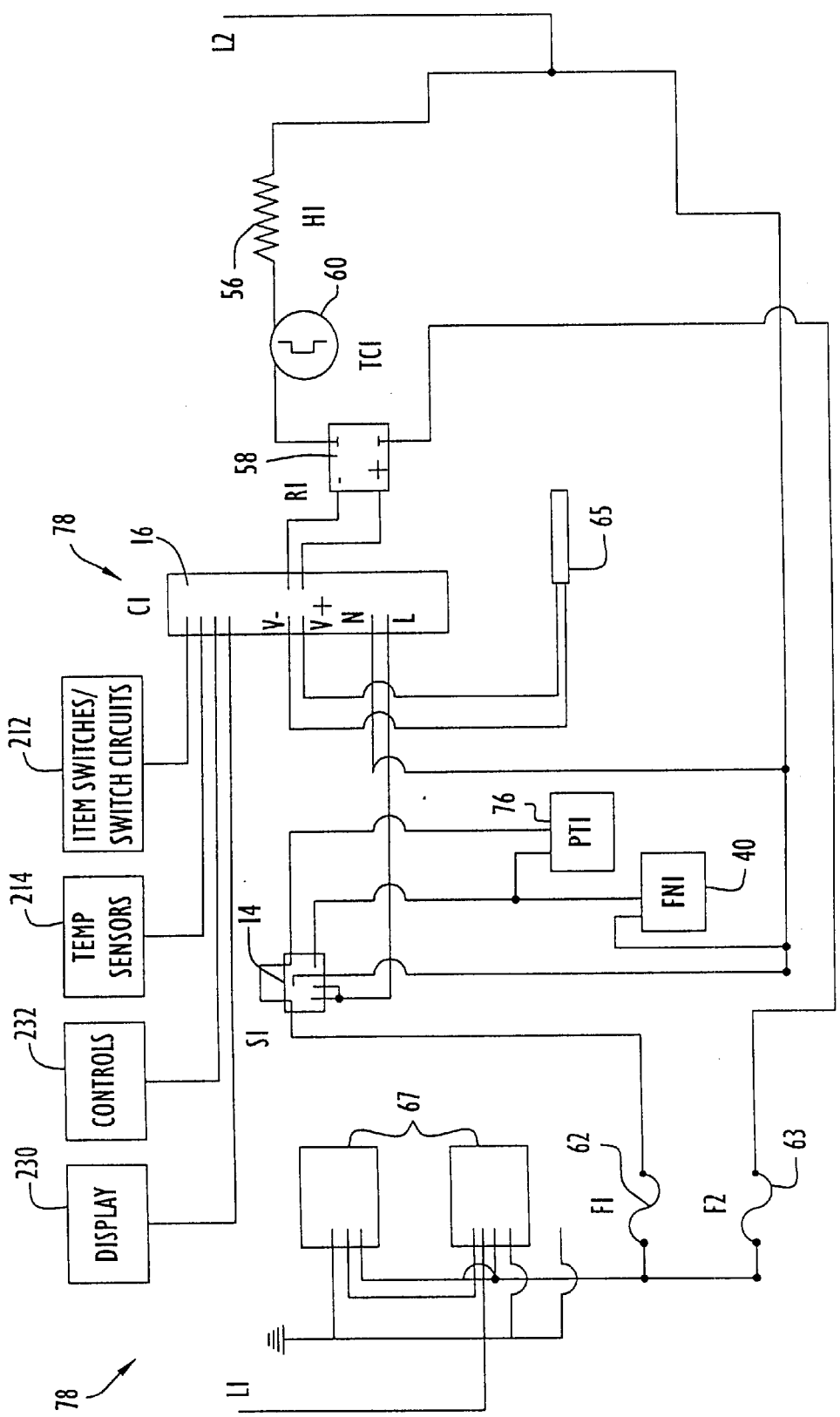
FIG. 9 is an electrical schematic diagram of an exemplary control circuit for the warmer unit of FIG. 1 according to the present invention.

Front panel 12 includes a power switch 14 and a temperature controller holder 15 typically disposed toward the upper portion of a front panel edge (e.g., the upper portion of a front panel rightmost edge as viewed in FIG. 1). Holder 15 is a pocket of substantially triangular cross-section with an open top portion to receive controller 16 (FIG. 9). The pocket may further include a connector (not shown) to couple the controller to system circuitry and/or devices. The power switch and holder (e.g., along with the controller) may alternatively be disposed on the warmer unit in any fashion capable of operating the warmer unit. Power switch 14 enables power to controller 16 and a fan disposed within the warmer unit described below to commence heating the compartment to a desired temperature. Controller 16 is typically implemented by a microprocessor and is coupled to and controls a display 230 typically disposed on front panel 12 below pocket 15. The display indicates various system and item information as described below. Controls 232 are disposed beneath display 230 on the warmer unit front panel to facilitate control of the display and entry of information into the controller as described below. Alternatively, the controller may include a display and input devices disposed thereon to display a compartment temperature and enable an operator to enter a desired temperature for the compartment.

Top panel 8 may further include an intravenous support or pole (not shown) to accommodate intravenous (IV) and/or irrigation fluid bags heated by warmer unit 2a for application to patients. The intravenous pole mounted on the warmer unit enhances efficiency by enabling immediate use of the warmed fluid since the pole and warmer unit are in close proximity. Moreover, top panel 8 may include a lamp or other light source (not shown) that illuminates the top panel such that an operator has sufficient light to transcribe information during a medical procedure. In addition, other items, typically utilized in an operating room, may be attached to warmer unit 2a to reduce consumption of operating room space.

Front panel 12 further includes a door 18 that enables access to compartment 24. Door 18 is substantially rectangular and is generally disposed within front panel 12 between power switch 14 and a front panel side edge (e.g., the leftmost side edge as viewed in FIG. 1). A substantially rectangular window 17, typically constructed of clear polycarbonate or other transparent material, is disposed on the door and includes dimensions slightly less than the door dimensions. Door 18 may vary in size according to the size of the warmer unit, and generally includes dimensions slightly less than front panel 12. The door is preferably connected to front panel 12 via hinges (not shown) disposed toward the door upper edges that enables the door to pivot upwards toward top panel 8. Further, door 18 includes a handle 30 disposed below window 17 and extending along a window bottom edge. Handle 30 is preferably implemented by an L-shaped handle that extends outward from an external surface of the door to enable an operator's hand to grip the handle and manipulate that door. Alternatively, handle 30 maybe implemented by any handle capable of manipulating the door. Door 18 is typically manipulated to an open position to enable a warmer unit tray or drawer described below to access the compartment, whereby the drawer contains medical items to be heated by the warmer unit. The surgical warmer unit components (e.g., panels, walls, plates, doors, etc.) are typically constructed of a suitably sturdy or rigid material, such as aluminum, but may be implemented by any material (e.g., metals, plastics, etc.) capable of accommodating the desired component function described herein.

Figure 2:
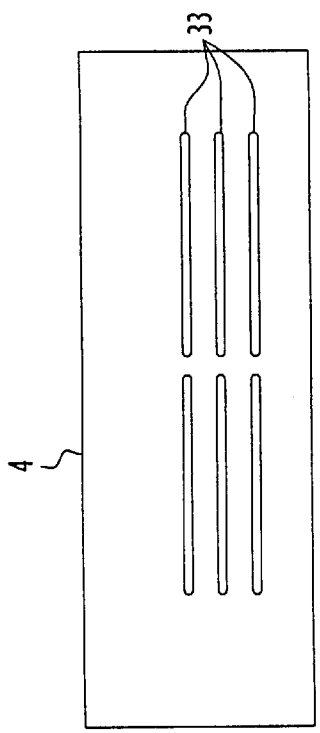
FIG. 2 is a view in elevation of a rear panel of the warmer unit of FIG. 1 according to the present invention.

The warmer unit rear panel is illustrated, by way of example only, in FIG. 2. Specifically, rear panel 4 is substantially rectangular as described above. A plurality of slots 33 is defined in the rear panel to permit air to enter the warmer unit to be heated for maintaining compartment temperature as described below. Slots 33 are generally elliptical slots having their major axes extending along the longer dimension of rear panel 4, whereby the major axes of the slots are substantially greater than the slot minor axes. Slots 33 are generally defined in rear panel 4 in groups of three rows (e.g., each row extends across the longer dimension of the rear panel) with each row having two adjacent slots, whereby a group of slots is disposed coincident compartment 24. However, rear panel 4 may include any quantity (e.g., at least one) of slots whereby the slots may be of any shape or size and may be arranged in any fashion capable of enabling air to enter the warmer unit.

Figure 3:
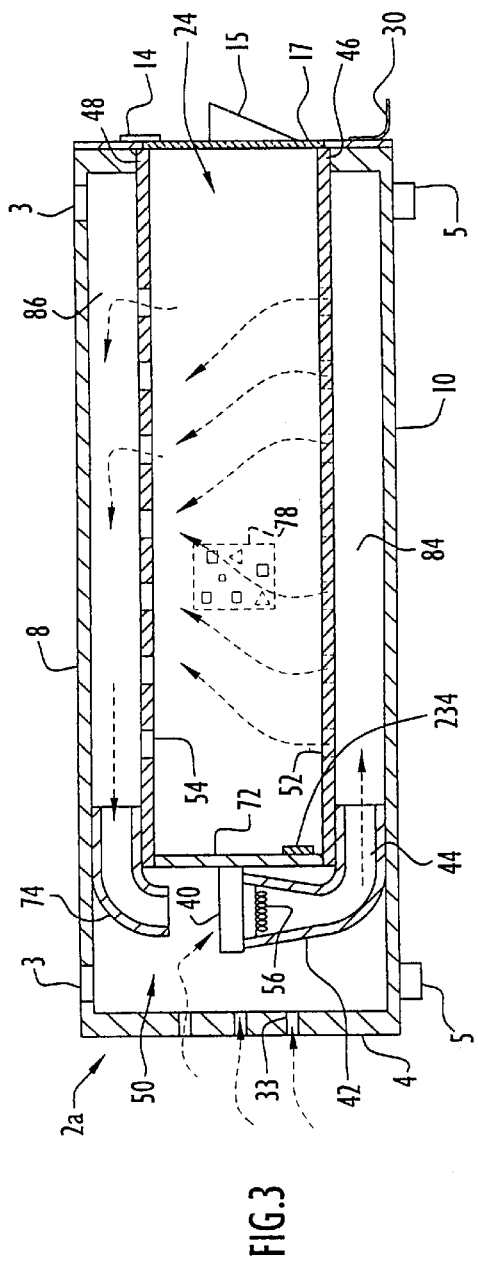
FIG. 3 is a side view in elevation and partial section of the warmer unit of FIG. 1 diagrammatically illustrating air flow paths through the warmer unit according to the present invention.

Referring to FIG. 3, compartment 24 includes side walls 70 (FIG. 1), a rear wall 72 and respective floor and ceiling plates 46 and 48. The compartment side and rear walls 70, 72 and floor and ceiling plates 46 and 48, respectively, are substantially rectangular wherein side walls 70 extend from front panel 12 toward rear panel 4, and from bottom panel 10 to top panel 8. Side and rear walls 70, 72 of compartment 24 are disposed about the peripheral edges of floor and ceiling plates 46 and 48 with rear wall 72 disposed between the floor and ceiling plates. The side and rear walls and the floor and ceiling plates collectively define a compartment interior wherein medical or other items may be heated. Floor and ceiling plates 46 and 48 have substantially similar dimensions and include holes defined in the respective floor and ceiling plates to permit air flow through the compartment as described below.

Compartment 24 is essentially in the form of a rectangular box wherein length and width dimensions of the compartment are similar, however, the length and/or width of side and rear walls 70, 72 may vary (e.g., thereby altering the compartment depth and height) to produce compartments of different sizes or capacities (e.g., FIG. 10). The length and width dimensions of compartment 24 are slightly less than the warmer unit interior length and width dimensions such that a short distance resides between side walls 70 and side panels 6, and between rear wall 72 and rear panel 4. In addition, a slight distance resides between compartment 24 and bottom panel 10, and between compartment 24 and top panel 8. The distances between the compartment and the bottom and top panels form lower and upper cavities 84, 86, respectively, that enable air flow through the compartment as described below. The lower and upper cavities are substantially rectangular and have dimensions substantially similar to respective floor and ceiling plates 46 and 48. The distance between compartment rear wall 72 and rear panel 4 serves as an air chamber 50 whereby outside air enters warmer unit 2a via slots 33 defined in the warmer unit rear panel as described above.

A heater in the form of a conventional fan 40 with a corresponding heating coil 56 is mounted on an exterior surface of rear wall 72 of compartment 24 and forces air from air chamber 50 and upper cavity 86 over the heating coil to produce heated air that heats items disposed within the compartment. Air from upper cavity 86 is received by fan 40 via an upper manifold 74 disposed proximate the upper cavity and extending toward the fan. The heated air flows through compartment 24 as described below whereby the heated air is recycled (e.g., re-used within that compartment) and mixed with outside air in various concentrations, depending upon the current compartment and desired temperatures, to control the compartment temperature. Compartment 24 further includes a thermocouple 65 (FIG. 9), typically implemented by a conventional or other type of temperature sensor, that measures the temperature within the compartment and sends a temperature signal to the controller as described below. The thermocouple is typically disposed within compartment 24 in one of the compartment side walls 70 at a height corresponding to approximately a middle height of the compartment.

Warmer unit 2a heats a mixture of outside or make-up air and recycled air (e.g., air previously utilized within the particular compartments) and forces the heated air to flow proximate a tray or drawer 34 (FIGS. 6a–6d) disposed within compartment 24 in order to heat the medical items contained within the drawer to a desired temperature. Fan 40 is disposed on an exterior surface of compartment rear wall 72 toward the uppermost portion of the compartment. Fan 40 draws air into the compartment from upper cavity 86 (e.g., via upper manifold 74) and air chamber 50, whereby air infiltrates the air chamber via rear panel slots 33 as described above. A duct 42 is disposed beneath fan 40 and receives air driven by the fan. Duct 42 is substantially trapezoidal (e.g., the duct includes a substantially trapezoidal cross-section) and extends from fan 40 toward lower cavity 84. The width of the duct gradually narrows from fan 40 toward the lower cavity whereby the duct is similar in configuration to a funnel. Duct 42 includes heating coil 56 disposed within the duct toward fan 40 to heat the air. The duct directs or funnels air over heating coil 56 and through a lower manifold 44 disposed at a distal end of the duct. The lower manifold directs the air through lower cavity 84 and into the compartment via floor plate 46 that is disposed above the lower cavity.

Figure 4:
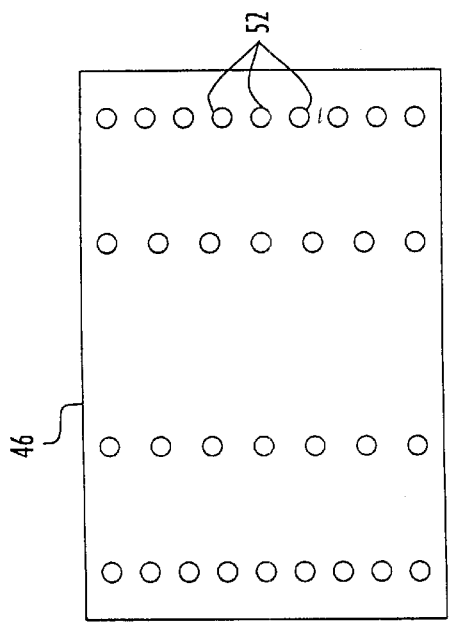
FIG. 4 is a top view in plan of a warming system compartment floor plate for directing heated air flow to enter a warming system compartment according to the present invention.

Referring to FIG. 4, floor plate 46 is substantially rectangular having length and width dimensions substantially similar to the compartment length and width dimensions whereby the floor plate includes a plurality of holes or apertures 52 defined within the floor plate. Holes 52 are typically arranged through floor plate 46 in four columns (e.g., as viewed in FIG. 4 with each column extending in a direction of the floor plate shorter dimension edges or floor plate transverse axis from the front to the rear of the compartment) with each column spaced a sufficient distance to encompass the floor plate surface whereby the hole columns disposed toward the floor plate shorter dimension edges each generally include a greater quantity of holes than the remaining columns. The holes enable heated air from lower cavity 84 (FIG. 3) to enter the compartment.

Figure 5:
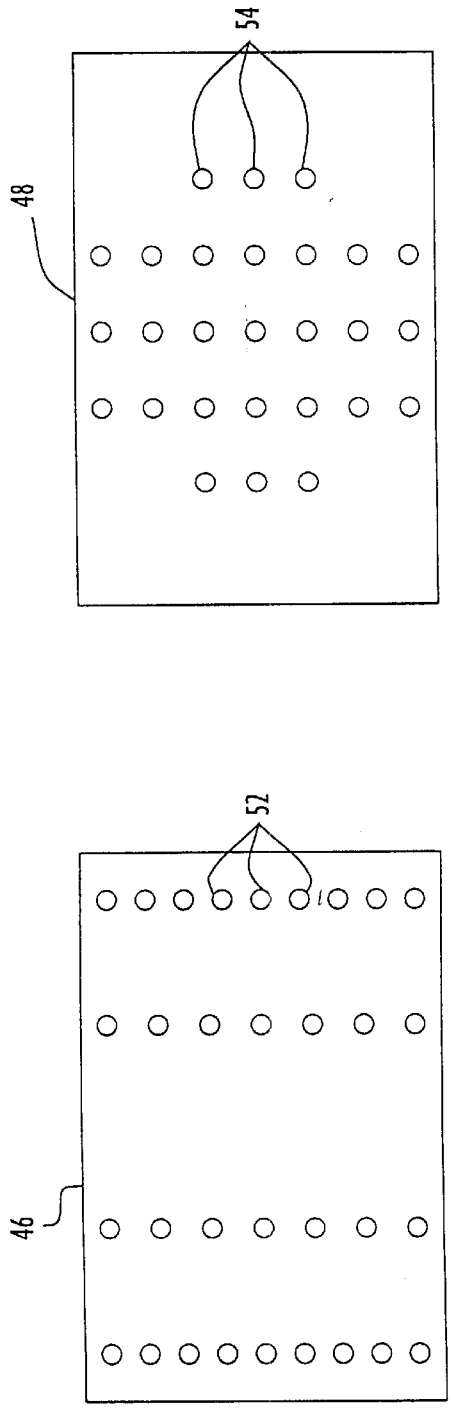
FIG. 5 is a top view in plan of a warming system compartment ceiling plate for directing heated air flow to exit a warming system compartment according to the present invention.

The heated air traverses compartment 24 and the drawer containing medical items to heat those items, and exits the compartment via ceiling plate 48 illustrated in FIG. 5. Specifically, ceiling plate 48 is substantially similar to floor plate 46 (FIG. 4) except that the ceiling plate includes a plurality of holes or apertures 54 defined within the ceiling plate in a different arrangement. Holes 54 are typically arranged through ceiling plate 48 in five columns (e.g., as viewed in FIG. 5 with each column extending in the direction of the ceiling plate shorter dimension edges or ceiling plate transverse axis from the front to the rear of the compartment) substantially evenly spaced and concentrated about the ceiling plate center whereby the hole columns disposed toward the ceiling plate shorter dimension edges each generally include a lesser quantity of holes than the remaining columns. Holes 54 defined in ceiling plate 48 enable heated air to exit the compartment into upper cavity 86 (FIG. 3). The ceiling plate typically includes a substantially lesser amount of holes than floor plate 46.

The particular arrangements of the holes within the floor and ceiling plates create a flume-like effect within the compartment to direct heated air toward the middle of the compartment. In other words, the heated air enters the compartment and is directed inwardly toward the middle of the compartment to prevent the heated air from flowing around the outside of the medical items contained within the drawer (e.g., to prevent greater heating around the edges by concentrating more of the air flow onto the drawer). The flume-like air flow within the compartment enables the air to efficiently and evenly heat the items contained within the compartment drawer. Air flow from the ceiling plate is received in the upper cavity disposed above the ceiling plate, whereby the air enters the upper manifold that directs the heated air back into the fan within the air chamber.

Referring back to FIG. 3, medical items are disposed within compartment 24 whereby heated air flow is distributed substantially evenly about items within the compartment to heat those items evenly to a desired temperature. Specifically, outside air infiltrates warmer unit 2a via slots 33 defined in rear panel 4 and flows into air chamber 50 whereby the outside air mixes with heated air flowing from the compartment. Fan 40 directs air from chamber 50 and upper manifold 74 through duct 42 whereby heating coil 56 disposed in the air flow path within the duct heats the air. The heated air is then directed into lower cavity 84 via lower manifold 44 whereby the air traverses the floor plate into the compartment. The air flows within the compartment in a flume-like fashion (e.g., as indicated by the arrows in FIG. 3) through drawer 34 (FIGS. 6a–6d) described below to heat items contained within the drawer, and exits the compartment via ceiling plate 48 into corresponding upper cavity 86. Upper manifold 74 directs the air from upper cavity 86 back to fan 40 within air chamber 50 to mix with fresh or make-up air and be recirculated into the compartment as described above to heat the medical items. The mixture of recycled and fresh air distributed to the compartment via fan 40 is controlled in a conventional manner based on the compartment and desired temperatures in order to efficiently maintain the compartment at the desired temperature.

Tray or drawer 34 for utilization within compartment 24 and for accommodating numerous medical solution containers in a generally upright position is illustrated in FIGS. 6a–6d. Initially, drawer 34 is typically disposed on runners or tracks (not shown) mounted on an interior surface of side walls 70 (FIG. 1) of compartment 24 that enable the drawer to smoothly slide into and out of the compartment. This sliding mechanism may be similar to that used in drawers within common desks. The drawer may further be removed from the runners or tracks and be replaced by another drawer of a different configuration for handling other types or sizes of medical items. Door 18 is typically manipulated to an open position to enable access to drawer 34 within compartment 24. Specifically, drawer 34 is similar to the drawer described in the aforementioned U.S. Pat. No. 6,294,762 and includes a generally box-like configuration including an upper frame 91 and a floor 93. Upper frame 91 and floor 93 are each substantially rectangular and have substantially similar dimensions. The upper frame includes front and rear bars 94, 96 and side bars 98, 99, each substantially rectangular and collectively defining a generally open upper frame interior to enable placement of items within the drawer. Floor 93 is aligned substantially coincident with upper frame 91 and includes front and rear bars 64, 66 and side bars 68, 69, each substantially rectangular and collectively defining a floor interior that is preferably constructed of wire mesh. Posts 92a–92d are each disposed toward a corresponding drawer corner to interconnect the frame to the floor. A support bar 95 extends along the shorter dimension edge of the floor and is attached to corresponding posts 92a, 92b. Similarly, a support bar 97 is disposed along the opposing shorter dimension edge of the floor and is attached to corresponding posts 92c, 92d. The support bars are each substantially rectangular and extend between the respective posts at a slight distance above floor 93 to structurally strengthen the drawer.

The drawer interior is partitioned into a plurality of receptacles 80, each for containing a medical solution container 35, such as an intravenous (IV) solution bag. The receptacles typically have sufficient storage capacity to accommodate container 35 in a generally upright position. In this fashion, drawer 34 may contain numerous medical solution containers or other medical items within compartment 24 for heating to a desired temperature. In order to form receptacles 80, drawer 34 includes a plurality of dividers that partition the drawer interior. In particular, drawer 34 includes transverse dividers 81 and longitudinal dividers 83. Transverse dividers 81 extend substantially in parallel between front and rear upper frame bars 94, 96, and are spaced apart along the upper frame longer dimension. Longitudinal dividers 83 extend substantially in parallel between upper frame side bars 98, 99 and are spaced apart along the upper frame shorter dimension. The transverse and longitudinal dividers are generally orthogonal to each other and essentially form a grid to partition the drawer interior into individual receptacles 80.

Figure 6A:
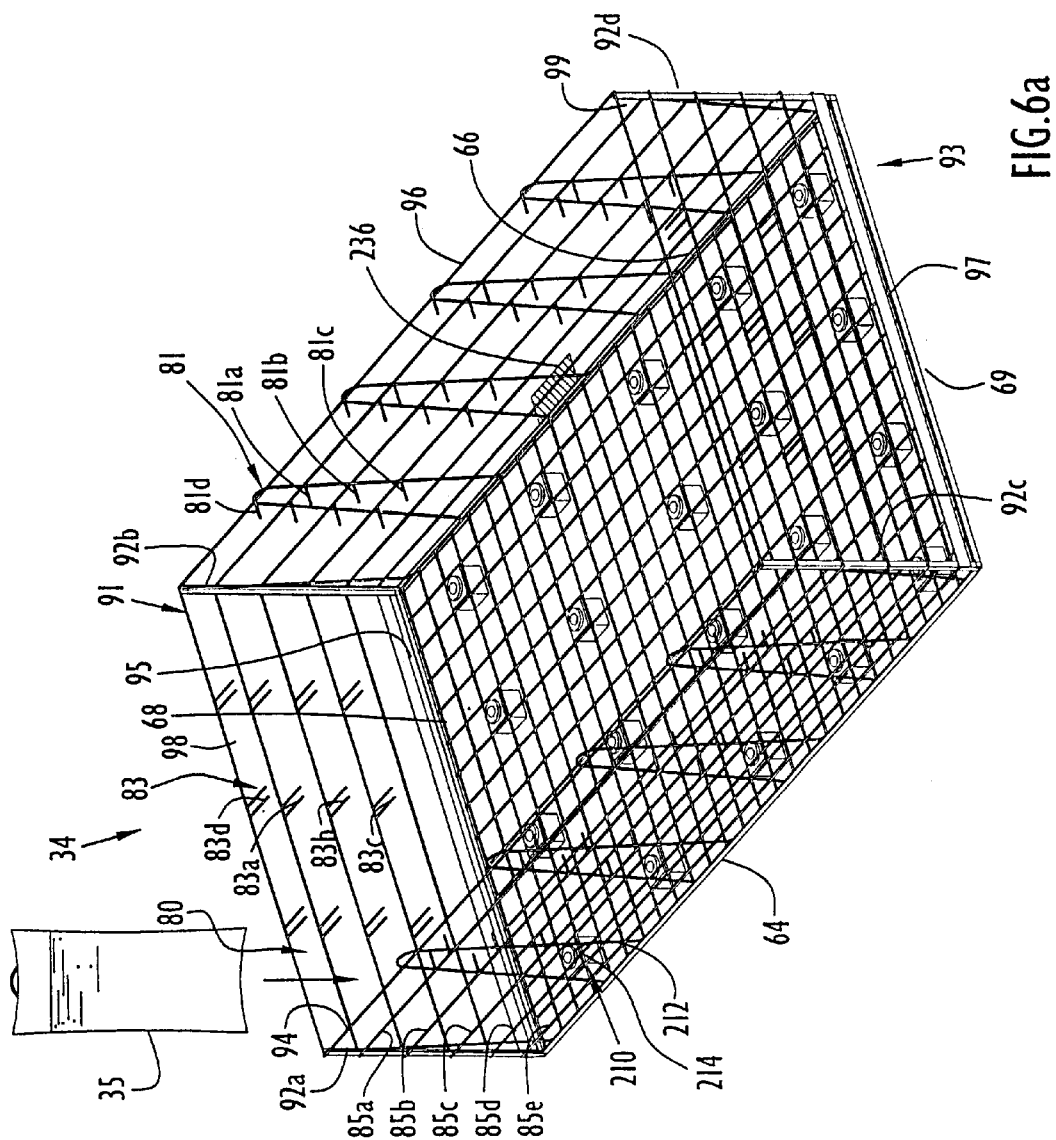
FIG. 6a is an exploded view in perspective of a tray or drawer including individual monitoring assemblies and a configuration to enable storage of numerous medical solution containers in a generally upright position according to the present invention.
Figure 6B:
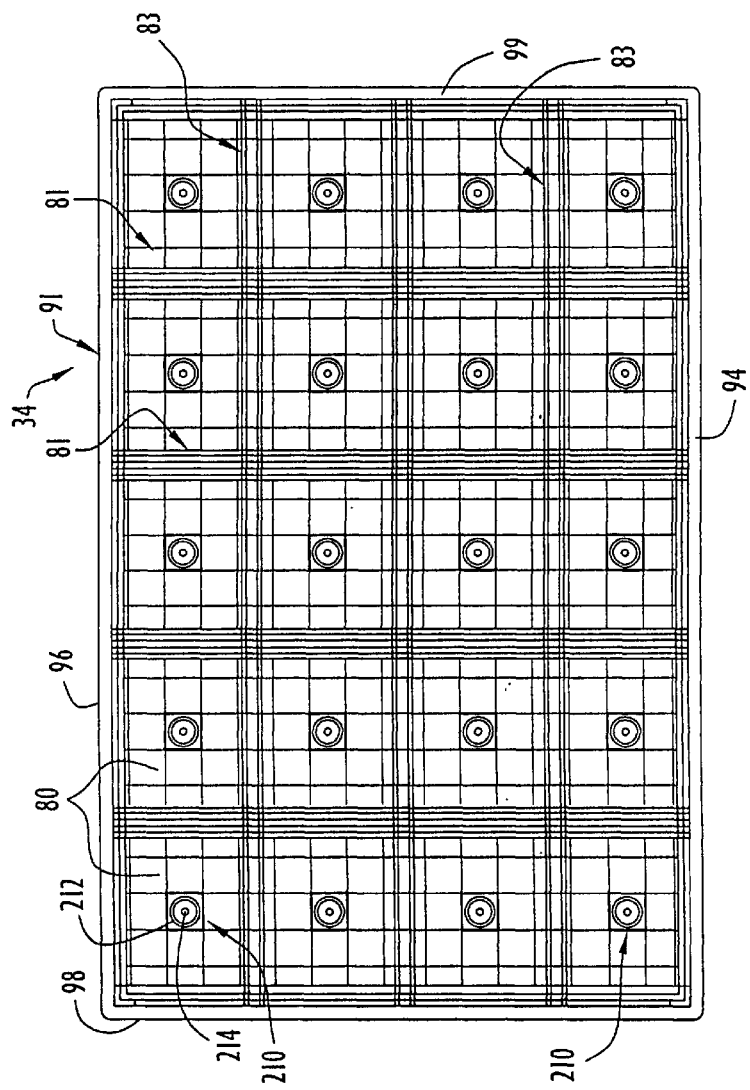
Figure 6C:
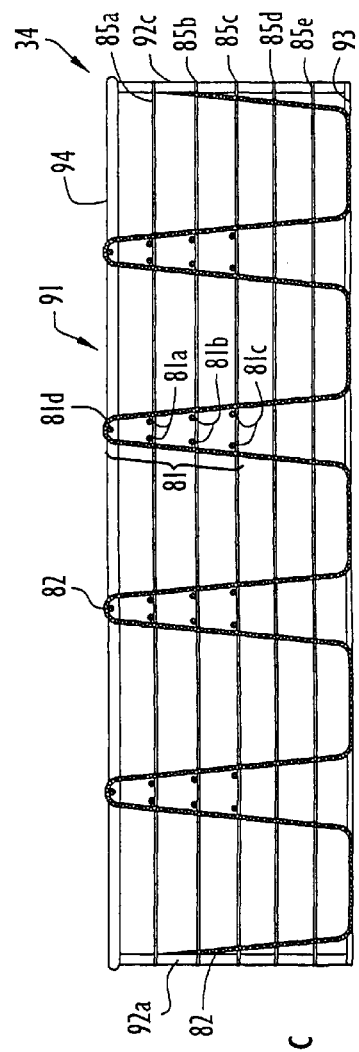

Transverse dividers 81 each include a series of wire members 81a–81d (FIG. 6c). Wire member 81d includes a single wire attached to and extending between front and rear upper frame bars 94, 96. Wire members 81a–81c each include a pair of horizontal wires extending substantially in parallel between front and rear upper frame bars 94, 96. Wire 81d forms the intersection of two planes tilted slightly from vertical, each plane including a respective wire from each of the wire pairs 81a–81c. The wires in each plane are spaced generally vertically and are oriented parallel to one another. The distance between wires in each wire pair 81a–81c successively increases as the wire pair position is further away from upper frame 91 and closer to floor 93. A series of peripheral wire members 85a–85e extend about the drawer periphery and are vertically spaced apart between the upper frame and floor. Wire members 81a–81c of each transverse divider 81 are vertically positioned between the upper frame and floor at locations corresponding to the vertical positions of respective peripheral wire members 85a–85c. A support wire member 82 extends along the drawer longer dimension between posts 92a, 92c and generally on the exterior side of the peripheral wire members, and has each end attached to a corresponding post. The support wire member repeatedly extends between the upper frame and floor in a generally wave-like pattern. In particular, the support wire member extends over each divider 81 and along floor 93 between dividers 81, between a divider 81 and post 92a and between a divider 81 and post 92c. The increased spacing between wire pair members of wire members 81a–81c and the single wire of wire member 81d provide the support wire member pattern with rounded peaks and substantially trapezoidal valleys. Support wire member 82 is attached to upper frame 91 and floor 93 proximate the peaks and valleys, respectively. Another wire member (not shown) is attached to and disposed in substantially the same manner between posts 92b, 92d along the drawer rear portion. Wire members 81a–81d of each transverse divider are connected to the support wire members at locations within the interior sections of the peaks that extend over the transverse dividers.

Figure 6D:
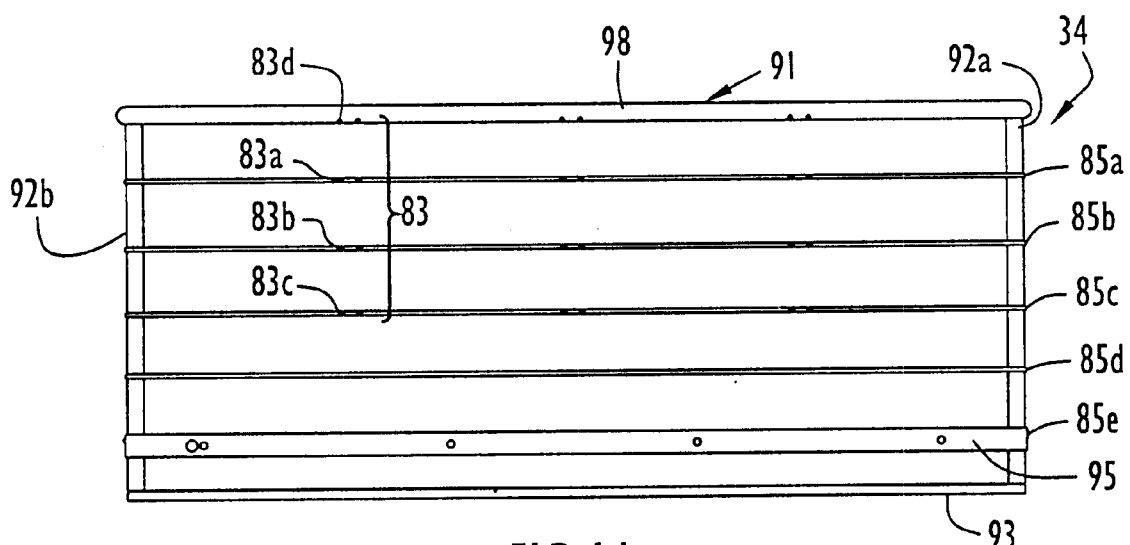

Longitudinal dividers 83 each include a series of wire members 83a–83d (FIG. 6d). Wire member 83d includes a pair of wires attached to and extending substantially in parallel between side bars 98, 99. Wire members 83a–83c similarly include a pair of horizontal wires extending substantially in parallel between bars 98, 99. Wire members 83a–83d are essentially contained within two parallel planes, each plane including a respective wire from each of the wire pairs 83a–83d. The wires in each plane are spaced generally vertically and are oriented substantially parallel to one another. The members of each wire pair are separated by substantially the same distance. Wire members 83a–83c of each longitudinal divider have their ends attached to corresponding peripheral wire members 85a–85c between respective posts 92a, 92b and 92c, 92d. The wire members are vertically positioned between the upper frame and floor at locations corresponding to the vertical positions of respective peripheral wire members 85a–85c.

The longitudinal divider wire members may extend over or under the transverse divider wire members within the drawer interior to partition the drawer interior into receptacles 80, each having sufficient storage capacity to contain medical solution container 35 in a generally upright position. The mesh floor enables heated air from the compartment to infiltrate the receptacles and heat the items contained therein. The upper frame, floor, posts and bars may be of any size or shape and may be constructed of any suitably sturdy or rigid material that can withstand the compartment temperature. In addition, the wire members of the dividers may be implemented by any wire, rope, cable, string or other line of any size or cross-sectional shape that can withstand the compartment temperature.

Drawer 34 may include any quantity of interchangeable receptacles that may be replaced with receptacles or groups of receptacles having different configurations for containing medical items of different types or sizes. The receptacles may each include a receptacle frame with the receptacle frame and/or transverse and longitudinal dividers including fasteners to removably secure the receptacles to the drawer. In addition, drawer 34 may alternatively have a configuration that is adjustable to include several receptacles as described above or a single large receptacle for accommodating large medical items, such as blankets. The transverse and longitudinal dividers may be disposed in sliding relation with posts 92a–92d between the upper frame and floor. When the transverse and longitudinal dividers are positioned adjacent floor 93, the drawer contains a single large receptacle, while positioning of the transverse and longitudinal dividers toward upper frame 91 forms individual receptacles 80. For examples of these and other types of drawers suitable for use with the warmer unit, reference is made to the aforementioned U.S. Pat. No. 6,294,762.

Drawer 34 may further include a series of monitoring assemblies to monitor the temperature and residence time (e.g., amount of time an item resides within the warmer unit) of individual medical items heated within the warmer unit. Specifically, monitoring assemblies 210 are each mounted below the approximate center of a receptacle floor portion of a corresponding receptacle 80, where the monitoring assemblies may be mounted to the drawer via any suitable mounting devices (e.g., clamps, brackets, adhesives, etc.). The compartment runners or tracks described above basically suspend the drawer and monitoring assemblies above the compartment floor. The monitoring assemblies each include an item sensor or switch 212 to detect when a medical item is placed within a corresponding receptacle 80 and a temperature sensor 214 to directly measure the temperature of the medical item within that receptacle. The item sensor is preferably a pressure type switch as described below, however, any type of proximity or other sensor (e.g., an optical or magnetic switch or sensor, etc.) may be employed to sense the presence of a medical item within a receptacle.

Figure 7:
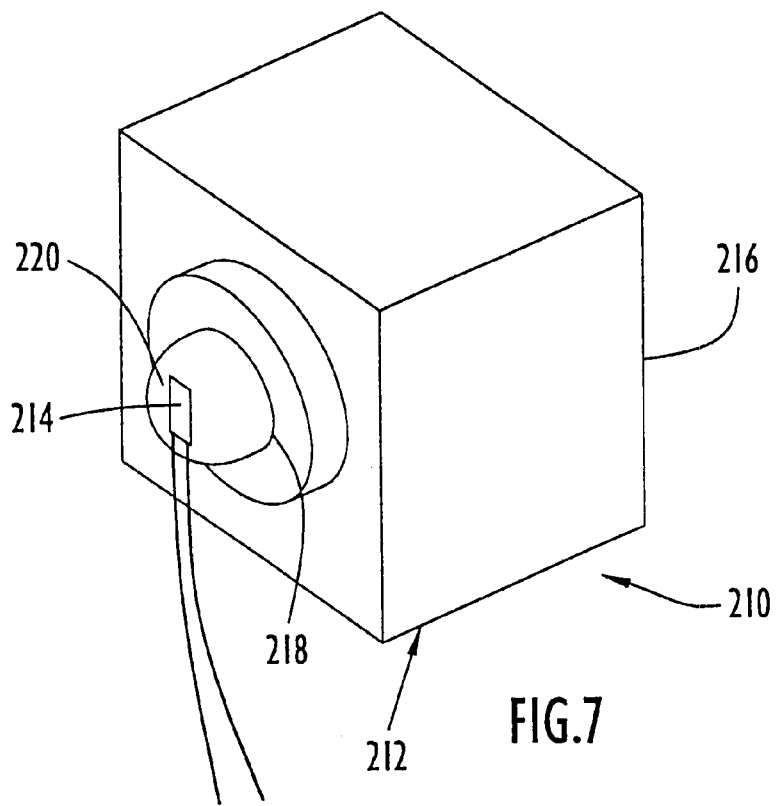

Referring to FIG. 7, item sensor or switch 212 includes a housing 216 mounted below a floor portion of a corresponding receptacle as described above and an actuable assembly 218 disposed on the housing top surface. Housing 216 includes a switch circuit (not shown) to provide a signal to controller 16 (FIG. 9) when the item switch is in a closed state. Actuable assembly 218 includes a resilient contact member 220 that is disposed in slidable relation with the actuable assembly and housing 216. The contact member protrudes distally from the actuable assembly and extends through the actuable assembly into housing 216 to interface the switch circuit. Temperature sensor 214 is disposed at the distal end of contact member 220 and may be implemented by a resistive temperature device (RTD) or any other suitable sensor (e.g., IR, NTC, thermistors, thermocouples, etc.) for measuring the temperature of a medical item disposed within the receptacle. The contact member and temperature sensor extend from housing 216 through an opening in the drawer mesh floor and into a lower central portion of a corresponding receptacle 80 in order to monitor a medical item within that receptacle.

The item switch basically serves as a momentary type switch with contact member 220 in the form of a plunger and movable into housing 216 to interface the switch circuit. The contact member effectively facilitates creation of an electrical path within the switch circuit and closure of the item switch to provide a signal to the warmer unit controller indicating the presence of a medical item within the receptacle. Specifically, in response to insertion of a medical item into a receptacle, the medical item contacts the distal end of contact member 220 and temperature sensor 214. The weight of the medical item forces the temperature sensor against the item and urges contact member 220 into housing 216 to interface the switch circuit. The contact member is typically biased by a resilient member (e.g., spring, etc.) (not shown) to be withdrawn from the switch circuit; however, the weight of the item overcomes this biasing force. When the contact member is forced to interface the switch circuit, the contact member basically forms an electrical path within the circuit (e.g., closing the switch circuit), thereby effectively closing the switch. The path enables the switch circuit to provide a signal to the controller indicating the presence of the medical item within the receptacle. Conversely, removal of the medical item from the receptacle results in withdrawal of contact member 220 from the switch circuit via the resilient member bias, thereby effectively disabling the electrical path within the switch circuit and opening the switch. This prevents the switch circuit from providing a signal to controller 16 and thereby indicating to the controller the absence of a medical item within the receptacle.

The temperature sensors and item sensors of the monitoring assemblies generally include wiring (not shown) that extends to a connector 236 disposed on a lower rear portion of drawer 34 (FIG. 6a). The drawer connector is typically coupled, via a suitable cable, to a corresponding warmer unit connector 234 (FIG. 3) disposed on warmer unit compartment rear wall 72. Controller 16 is coupled to connector 234 via wiring (not shown). The cable basically maintains coupling between the drawer and warmer unit connectors and, hence, between the controller and monitoring assemblies, during insertion and removal of the drawer within the compartment. Alternatively, the drawer and warmer unit connectors may directly engage and/or disengage each other manually and/or automatically in response to drawer insertion and/or removal.

Figure 8:
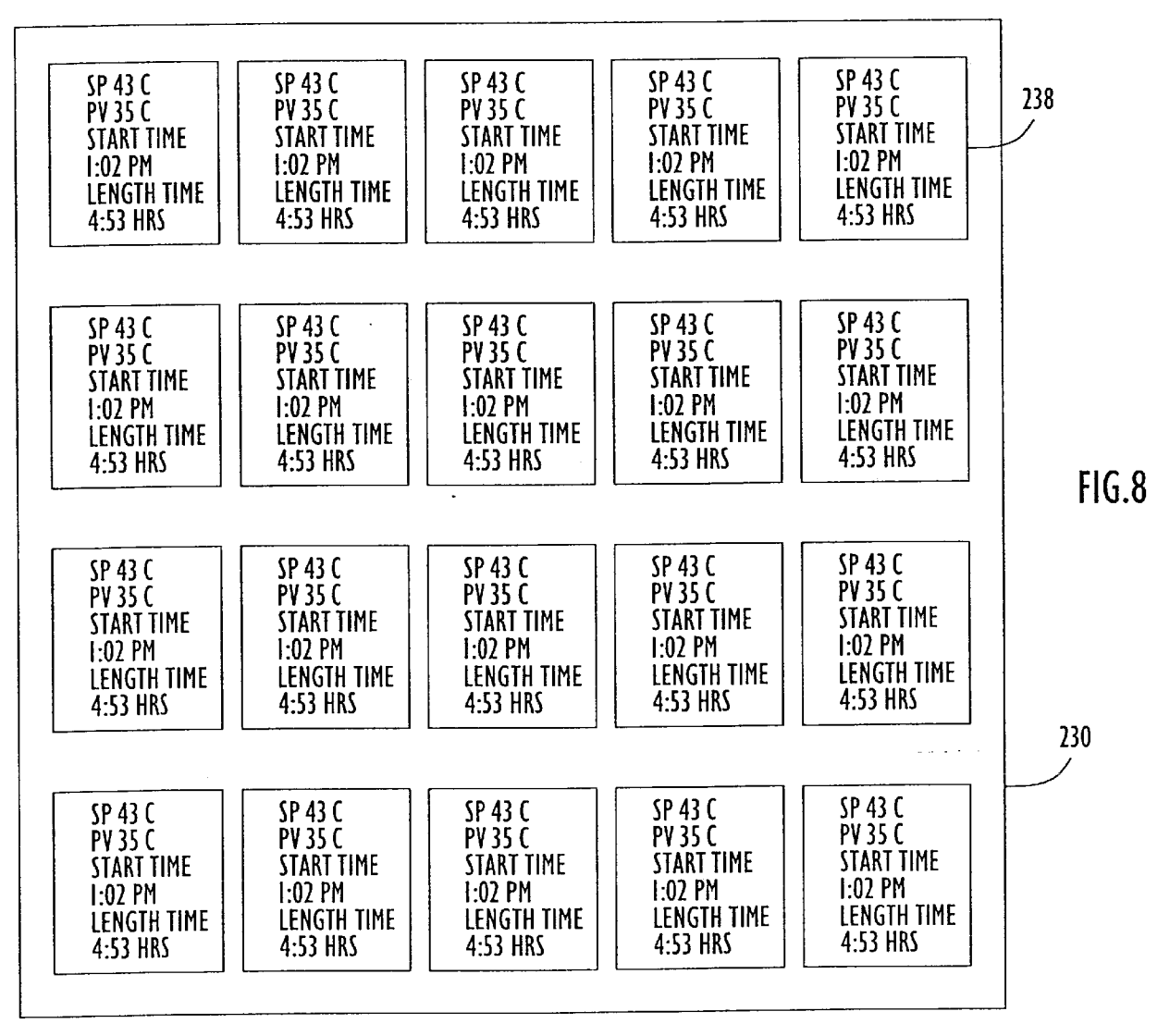

Temperature controller 16 of warmer unit 2a receives and processes signals from the monitoring assemblies and controls display 230 to provide various information as illustrated in FIGS. 1 and 8. Specifically, controller 16 receives signals from the switch circuits of the monitoring assemblies in response to placement of medical items within the receptacles as described above. When an initial switch circuit signal is received indicating placement of a new item within a corresponding receptacle, the controller determines and stores the time (e.g., start time) the item is placed in the receptacle. The controller further maintains residence time for the medical item based upon subsequent signals received from the switch circuit. Basically, the controller maintains the residence time until cessation of the switch circuit signal, thereby indicating removal of the item. The controller typically polls lines from the switch circuits periodically to determine the presence of switch circuit signals and, hence, medical items within the receptacles. The controller includes a series of counters each associated with a corresponding receptacle, where a counter is initiated in response to initial reception of a corresponding switch circuit signal (e.g., a corresponding switch enters a closed state) and is reset (e.g., to a zero value) when the switch circuit signal is no longer received (e.g., the corresponding switch enters an open state). Thus, each counter maintains a residence time while a medical item is retained within a corresponding receptacle. The count or total of the counter indicates actual time and may be converted to any desired units (e.g., seconds, minutes, hours, etc.) based on a controller system clock rate. The temperature and start and residence times for the medical items are indicated by display 230 as described below. Controls 232 are typically in the form of buttons and facilitate entry of information into the controller associated with the receptacles. In particular, controls 232 enable entry of a set point or desired temperature for the compartment and medical items contained therein and facilitate control of display 230 (e.g., the display format, information to display, etc.). A single set point temperature is typically entered for the compartment and applies to all drawer receptacles. Alternatively, set point temperatures maybe independently entered for the compartment and each drawer receptacle. The controls may also facilitate entry of any other desired information to the controller (e.g., maximum residence times for the medical items, etc.). The controller is configured to store the set point and/or other information relating to the receptacles and may further receive and display information via controller display and input devices (not shown) as described above.

Display 230 is preferably an LCD or LED type display and provides information within an array of bordered fields 238 each associated with a corresponding receptacle 80. The display fields and receptacles maybe identified in any suitable manner (e.g., assigning a number or other identifier to each display field and corresponding receptacle, etc.) to allow a user to readily associate a particular display field with a corresponding receptacle. Each display field 238 includes for a corresponding receptacle the entered set point temperature, an actual temperature of the medical item as measured by the corresponding monitoring assembly temperature sensor, and start and residence times (e.g., displayed in hours and minutes) for the medical item. Byway of example only, a display field 238 (e.g., as viewed in FIG. 8) indicates for a medical item within a corresponding receptacle a set point temperature of 43° C., an actual item temperature of 35° C., a start time of 1:02 PM and a residence time of four hours fifty-three minutes. The controller typically controls display 230 to provide the information for only those receptacles containing a medical item as indicated by the corresponding monitoring assemblies. However, the controller may further provide information for those receptacles lacking a medical item. In this case, the above-described information for such receptacles may include start and residence times having initial values (e.g., zero), and an actual temperature reflecting the compartment temperature as measured by the corresponding monitoring assembly temperature sensor. The controller updates the data displayed in display fields 238 in response to the counters, monitoring assemblies 210, controls 232 and/or the controller input devices. Display 230 may provide any desired information relating to the system and/or items in any desired format (e.g., an indication relating to whether or not a maximum heating time has been exceeded for a particular medical item, an indication relating to which receptacles within a drawer are vacant and/or occupied, time, date, etc.).

In addition, the warmer unit may include any suitable indicator to notify a user when a medical item has exceeded the set point temperature. In particular, display 230 may identify a receptacle containing a medical item exceeding the set point temperature via any suitable visual identifier (e.g., flashing field, bold field, arrows, display receptacle identifier, etc.). Further, the warmer unit may include an audio indicator or alarm (e.g., beep or other sound, speech synthesis, synthesized or recorded speech indicating receptacle identifier, etc.) to identify the receptacle containing a medical item exceeding the set point temperature. The visual and audio indicators may be utilized individually or in any combination to notify the user.

A control circuit 78 for controlling the warmer unit compartment to heat medical items is illustrated in FIG. 9. Specifically, control circuit 78 is typically mounted on a warmer unit side panel in the space between that side panel and a corresponding side wall of the warmer unit compartment. Control circuit 78 includes power switch 14 connected in series with compartment fan 40, a purge timer 76 and temperature controller 16. Switch 14 is operator controlled and enables activation of fan 40 and controller 16 whereby fan 40 may be implemented by conventional blowers or fans that direct air over heating coil 56 and through the compartment as described above. Purge timer 76 enables activation of fan 40 for approximately three to five minutes subsequent to switch 14 disabling operation of the warmer unit to dissipate heat from and cool heating coil 56 in order to prevent damage to the warmer unit from excessive heat.

Temperature controller 16 is typically implemented by a microprocessor controller, for example, model 2132 proportional-integral-derivative (PID) controller manufactured by Eurotherm Controls, Ltd. of England. The controller typically displays and receives information via display 230 and controls 232 as described above. However, controller 16 may include a display and enable an operator to set a desired compartment temperature via controller input devices or buttons (e.g., that modify control parameters, such as temperature, mode of operation, etc.) as described above. The controller display typically provides the compartment temperature via signals received from thermocouple 65 disposed within the compartment as described above. Thus, the controller is essentially a microprocessor, generally pre-programmed with its own software, that senses and controls compartment temperature in accordance with PID control and facilitates display of various system and item information to the user.

Controller 16 is connected to thermocouple 65 and in series with a solid state relay 58 that receives logic signals from the controller to close that relay and enable operation of heating coil 56 in accordance with the difference between the selected and existing compartment temperatures. Controller 16 essentially utilizes PID control to adjust the current through heating coil 56 via relay 58 to maintain the compartment at a desired temperature based on the desired and current compartment temperatures. Controller 16 is further connected to monitoring assemblies 210 (e.g., temperature sensors 214 and item switches 212 and/or the switch circuits), controls 232 and display 230 to provide temperature and start and residence time information as described above. The controller may further determine and display an estimated time required to heat a particular medical item disposed within a receptacle to a set point temperature based upon certain measured or known parameters (e.g., the measured temperature of the item, the rate of heat transfer within the compartment, etc.) and/or other parameters (e.g., the heat capacity and dimensions of the medical item, etc.) that may be entered into the controller. The estimated heating time may be indicated on display 230 within a corresponding field 238.

Heating coil 56 is disposed in series with solid state relay 58, and receives current from that relay to dissipate heat in order to heat the air within duct 42 (FIG. 3). High limit or overload switch 60 is connected between and in series with solid state relay 58 and heating coil 56, and enters an open state to disable the heating coil by shunting excess current from the heating coil when the current exceeds a threshold level (e.g., a level that may damage the warmer unit or circuit). Switch 14 and solid state relay 58 are connected in series with corresponding fuses 62, 63, respectively, to protect the circuit from excess current. Fuses 62, 63 are in turn connected in series with power receptacles 67. The receptacles typically receive power from a common wall outlet jack via a detachable power cord (not shown). The various control circuit components are typically implemented via conventional or commercially available components and/or may be implemented by any circuitry based on the functional description of the circuit described above.

Operation of the warmer unit is described with reference to FIGS. 1, 3, 6a and 9. Specifically, power switch 14 is actuated to enable operation of control circuit 78 and fan 40 to direct air over heating coil 56 and through the compartment as described above. Controller input devices (e.g., buttons) and/or controls 232 are manipulated to enter the set point and other information into the controller to maintain the compartment at the desired temperature, typically in the approximate range of 86° F.–104° F. The controller controls the heating coil as described above in accordance with the compartment temperature measured by thermocouple 65 to maintain the compartment at the desired temperature. Various medical items, such as intravenous or irrigation fluids, blood, instruments or drugs, are selected to be placed within individual receptacles 80 of drawer 34. Drawer connector 234 is coupled to warmer unit connector 236 via the cable and upon insertion of a medical item within a receptacle, the medical item engages corresponding temperature sensor 214 at the bottom of the receptacle and closes corresponding item switch 212. The drawer is subsequently inserted into the compartment, while the switch closure indicates the presence of the medical item to the controller as described above.

The controller subsequently determines the start time and initiates a residence time counter for each receptacle containing a medical item, while the temperature of each medical item is directly measured by a corresponding temperature sensor 214. The various temperatures and start and residence times for each medical item are displayed within corresponding display fields 238 of display 230 as described above. The controller updates display 230 and compares the measured temperature of each medical item with the set point temperature. When a measured temperature of a medical item exceeds the set point temperature, a visual and/or audio indication is provided by the warmer unit to notify a user that the medical item has exceeded the set point temperature as described above.

When medical items have attained the desired temperature, the drawer is retrieved from the compartment and the items are removed from the drawer for use in a medical or other procedure. In response to removal of a medical item from the receptacle, the corresponding item switch enters an open state, resulting in resetting of the corresponding residence time counter. The drawer may be inserted back into the compartment to facilitate continued heating of any other medical items that have not yet achieved the set point temperature. Further, a new medical item may be inserted into the receptacle from which the previous medical item was removed, while any additional information may be entered for the new medical item.

An exemplary warming system including multiple warmer units is illustrated in FIG. 10. Specifically, warming system 90 includes warmer units 2a, 2b 2c arranged in stacked relation. Warmer unit 2a is substantially similar to and functions in substantially the same manner as the warmer unit described above for FIG. 1. Similarly, warmer units 2b, 2c are substantially similar to and function in substantially the same manner as warmer unit 2a except that warmer units 2b, 2c include slightly greater dimensions to accommodate larger sized or greater quantities of items. For example, warmer unit 2b includes dimensions greater than warmer unit 2a, while warmer unit 2c includes dimensions greater than warmer unit 2b. Warmer units 2a, 2b, 2c include respective compartments 24, 26, 28, and are individually controlled to maintain those compartments at desired temperatures in substantially the same manner described above. The warmer units are typically vertically arranged, by way of example only, with warmer unit 2a disposed as the top unit, warmer unit 2c disposed as the bottom unit, and warmer unit 2b disposed between warmer units 2a, 2b. Feet 5 of each warmer unit are inserted within slots 3 of the warmer unit disposed adjacent and below that unit to securely arrange the warmer units in stacked relation. Each warmer unit includes at least one appropriately sized drawer 34 to enable items to be placed and removed within the corresponding compartment as described above. Warming system 90 may include any quantity of any sized warmer units whereby the warmer units may be selectively added or removed to the warming system. Thus, the warming system storage capacity may be adjusted to accommodate various quantities or sizes of items for particular applications. Further, any individual warmer unit or combination of warmer units within warming system 90 may be actuated to heat items depending upon the size or quantity of items required to be heated. In addition, warming system 90 may simultaneously heat various items to different temperatures. For further examples of the structure and operation of a stacked warming system, reference is made to the aforementioned U.S. Pat. No. 6,294,762.

The surgical warmer unit or warming system described above may be utilized in conjunction with an intravenous (IV) warming apparatus, such as an apparatus that heats intravenous solution as the solution is delivered to the patient from an intravenous bag or other container. Initially, the temperature of intravenous solution contained within an intravenous bag is generally unknown, within thirty degrees Fahrenheit or more, when the bag is hung on an intravenous rack or pole. The surgical warmer unit or warming system permits pre-heating of an intravenous solution bag to a desired temperature such that, upon removal from the warmer unit or warming system, the bag may be placed into a heated intravenous warmer suspended proximate a patient. Further, the warmer unit or warming system may also be used in combination with a thermal treatment machine having a basin for heating solutions, such as the machine disclosed in U.S. Pat. No. 5,333,326 (Faries, Jr. et al), the disclosure of which is incorporated herein by reference in its entirety. In this instance, bags or bottles of various solutions, such as irrigation fluid, may be placed in the warmer unit or warming system to be heated to a desired temperature. The heated bag or bottle is removed from the warmer unit or warming system with the contained solution at the desired temperature, and the solution is placed in the basin for available use more quickly during a surgical procedure since the solution is already heated to a temperature near its operational temperature.

Generally, the surgical warmer unit or warming system is set to heat the intravenous or irrigation solutions to temperatures slightly below their end use or operating temperatures, thereby making it is easier for the intravenous warmer or basin to warm the solutions to their desired operating temperatures. The warmer unit or warming system temperatures are typically set slightly below the solution operating temperature since it is easier to additionally warm the liquid in use within the intravenous warmer and thermal treatment machine rather than wait for the solutions to cool to the appropriate operating temperature. Thus, the intravenous or irrigation fluid heating time within the intravenous warmer and thermal treatment machine, respectively, is drastically reduced by use of the warmer unit or warming system.

Alternatively, warming system 90 may be implemented as a single cabinet structure having multiple heating compartments. An exemplary surgical warming system or cabinet 102 having a single cabinet structure is illustrated in FIG. 11. Specifically, cabinet 102 includes a rear panel 104, two substantially similar side panels 106, a top panel 108, a bottom panel 110 and a front panel 112. The top, side, front, rear and bottom panels are each substantially rectangular and define a cabinet interior wherein various medical or other items maybe heated. Cabinet 102 includes a plurality of individual heating compartments 124, 126, 128 each substantially similar to the compartment described above for warmer unit 2a, except that the cabinet includes a common chamber for re-cycling air and distributing air to the respective compartments. Each compartment is controlled by a corresponding process controller 116(1)–116(3), disposed on top panel 108, that is independent of process controllers associated with other compartments. Controllers 116(1)–116(3) are each substantially similar to controller 16 described above. Each compartment 124, 126, 128 typically includes a separate heating (i.e., temperature) range and may be set and maintained at a desired temperature independent of the other compartments. By way of example only, cabinet 102 includes three independent compartments disposed within the cabinet interior for heating medical or other items, however, the cabinet may include any number of independently controlled compartments.

Top panel 108 includes control switches 114(1)–114(3) and temperature controllers 116(1)–116(3) typically disposed toward a top panel edge (e.g., the top panel rightmost edge as viewed in FIG. 11) whereby a switch and controller correspond to each cabinet compartment to enable the compartments to be individually controlled. The switches and controllers may alternatively be disposed on the cabinet in any fashion capable of operating the cabinet. Switches 114(1)–114(3) enable power to a corresponding controller 116(1)–116(3) and a corresponding fan disposed within the cabinet to commence heating of a particular compartment to a desired temperature as described above. Controllers 116(1)–116(3) are each typically implemented by a microprocessor that is coupled to a corresponding display 230(1)–230(3) and responsive to corresponding controls 232(1)–232(3) as described below. However, the microprocessor may include a display and input devices to display a current temperature of an associated compartment and enable an operator to set a desired temperature for that compartment as described above. A main power switch (not shown) is typically disposed on a side panel 106 to enable operation of the entire cabinet. Top panel 108 may further include an intravenous support or pole (not shown) as described above to accommodate intravenous (IV) and/or irrigation fluid bags heated by warming cabinet 102 for application to patients. The intravenous pole mounted on the cabinet enhances efficiency by enabling immediate use of the warmed fluid since the pole and cabinet are in close proximity. Moreover, top panel 108 may include a lamp or other light source (not shown) as described above to illuminate the top panel such that an operator has sufficient light to transcribe information during a medical procedure. In addition, other items, typically utilized in an operating room, may be attached to cabinet 102 to reduce consumption of operating room space.

Front panel 112 includes a plurality of doors 118, 120, 122, that each enable access to respective cabinet compartments 124, 126, 128. Doors 118, 120, 122 are substantially rectangular and are disposed vertically adjacent each other with each door disposed within front panel 112 between side walls 170 of its corresponding compartment. Displays 230(1)–230(3) and controls 232(1)–232(3) are disposed adjacent respective doors 118, 120, 122 on front panel 112 to display information (e.g., temperature, start and residence times, etc.) and facilitate entry of information in substantially the same manner described above for warmer unit 2a. The warmer cabinet compartments may vary in size or capacity as described above, whereby compartment 128 may include the largest capacity, while compartment 124 may include the smallest capacity. The varying compartment capacities enable different sized items to be heated whereby larger items maybe disposed within compartment 128, while smaller items are typically disposed within compartment 124. However, items may be disposed in any compartment having sufficient capacity to accommodate that item. Similarly, doors 118, 120, 122 vary in size according to their corresponding compartments and have dimensions substantially similar to their corresponding compartment rear walls 172. The compartments each receive a corresponding drawer 34 of appropriate dimensions to heat medical items therein.

Cabinet 102 may be either stationary or mobile wherein the cabinet may include wheels or casters 132, preferably having selectively actuable locking mechanisms. Wheels 132 may be attached to bottom panel 110 for enabling the cabinet to be transported to various locations. The surgical warming cabinet components are typically constructed of a suitably sturdy or rigid material, such as aluminum, but maybe implemented by any material (e.g., metals, plastics, etc.) capable of accommodating the desired component function described herein. For further examples of the structure and operation of a cabinet system, reference is made to the aforementioned U.S. Pat. No. 6,294,762.

It will be appreciated that the embodiments described above and illustrated in the drawings represent only a few of the many ways of implementing a warming system and method for heating various items utilized in surgical procedures.

The warmer unit may be of any size or shape and may be constructed of any suitable materials. Air flow within the warmer unit may be directed toward items in any manner capable of heating the items via any suitable or conventional devices. The warmer unit may include any quantity (e.g., at least one) of compartments of any shape or size. The warmer unit door may be of any quantity (e.g., at least one), shape or size, may pivot in any fashion, and may be disposed anywhere on the warmer unit in any fashion capable of permitting access to the warmer unit compartment. The warmer unit door may be disposed on the warmer unit via hinges or any other mechanisms. Further, the warmer unit door may include any type of handle or other mechanism enabling opening and closing of the door, while the handle may be of any quantity (e.g., at least one), shape or size, and may be disposed on the door at any location and in any fashion. The door window may be of any shape or size, may be disposed on the door at any location in any fashion, and maybe constructed of polycarbonate or any other suitable and transparent material. Alternatively, the door may be utilized without a window, or with a translucent or opaque window.

The warmer unit power switch may be implemented by any conventional or other type of switch, button, relay or other device, and maybe disposed anywhere on the warmer unit in any fashion. The controller holder may be of any quantity (e.g., at least one), shape or size, and may be disposed anywhere on the warmer unit. Alternatively, the controller may be directly embedded within the warmer unit at any location. The warmer unit rear panel slots may be disposed anywhere on the rear panel or warmer unit and may be of any quantity (e.g., at least one), shape or size. Any devices may be disposed on the warmer unit (e.g., intravenous pole, light, etc.) at any location to aid in activities prior, during or after surgical procedures.

The warmer units maybe arranged in any fashion (e.g., vertically, horizontally, etc.), and may be of any quantity (e.g., at least one) to form a multiple unit warming system. The warmer unit slots and feet may be of any quantity (e.g., at least one), shape or size, and may be disposed anywhere on the warmer unit in any fashion to securely arrange the warmer units. Further, the warmer units may include any type of fastening or securing mechanisms to secure the warmer units in any configuration. The warmer unit feet may further include wheels, rollers or other devices to enable warmer units to be transportable, while the transport devices may include locking mechanisms to maintain a warmer unit in place.

The warming cabinet may be of any shape or size and may be constructed of any suitable materials, while the warming cabinet compartments may be of any quantity (e.g., at least one), shape or size. Air flow within the warming cabinet compartments may be directed toward items in any manner capable of heating the items via any conventional or suitable devices. The warming cabinet compartments may be arranged in any fashion (e.g., vertically, horizontally, etc.) such that any sized compartment may be disposed anywhere on the cabinet. The warming cabinet doors may be of any quantity (e.g., at least one), shape or size, may pivot in any fashion, and may be disposed anywhere on the warming cabinet in any fashion capable of permitting access to the compartments. The warming cabinet doors may be disposed on the warming unit via hinges or any other mechanisms. Further, the warming cabinet doors may include any types of handles or other mechanisms enabling opening and closing of the doors, while the handles may be of any quantity (e.g., at least one), shape or size, and may be disposed on the doors at any location and in any fashion. The doors may include a window of any shape or size that may be disposed on the door at any location in any fashion. The window may be constructed of polycarbonate or any other suitable materials.

The power switches of the warming cabinet may be implemented by any conventional or other types of switches, buttons, relays or other devices, and maybe disposed anywhere on the warming cabinet in any fashion. The controllers may similarly be disposed anywhere on the warming cabinet. The warming cabinet rear panel slots may be disposed anywhere on the rear panel or warming cabinet and may be of any quantity (e.g., at least one), shape or size. Any devices may be disposed on the warming cabinet (e.g., intravenous pole, light, etc.) at any location to aid in activities prior, during or after surgical procedures.

The manifolds and ducts of the warmer unit and warming cabinet may be implemented by any conventional or other types of manifolds, ducts, tubes or other devices capable of directing air flow. The manifolds and ducts maybe disposed in any manner proximate or within the warmer unit and warming cabinet to recycle air through the warmer unit and warming cabinet compartments. The manifolds and ducts may be of any quantity (e.g., at least one), shape or size, and may be constructed of any suitable materials. The heating coils of the warmer unit and warming cabinet may be implemented by any conventional or other type of heating element or device capable of heating air, and may be disposed within the warmer unit and warming cabinet at any location. Further, the warmer unit and warming cabinet may alternatively include any conventional or other type of heating device to warm the items.

The ceiling and floor plates of the warmer unit and warming cabinet may be of any quantity (e.g., at least one), shape or size, maybe disposed in any fashion within the warmer unit and warming cabinet compartments to direct air flow, and may be constructed of any suitable materials. The floor and ceiling plates may include any quantity (e.g., at least one) of holes of any shape or size arranged in any configuration to direct air within the warmer unit and warming cabinet compartments.

The tray or drawer described above and utilized within the warmer unit and warming cabinet compartments may be of any quantity (e.g., at least one), shape or size, may be implemented by any tray, drawer, carrier or other device capable of holding items within the compartment, and may be constructed of any suitable materials. The tray or drawer may include any quantity of bins, receptacles or other containers of any shape or size to contain any items at any desired orientations. The receptacles may each accommodate any quantity of any type of item. The tray or drawer may be placed within and removed from the warmer unit and warming cabinet compartments via any suitable mechanisms (e.g., tracks, runners, rollers, etc.). Further, the tray or drawer may accommodate any types of items for heating. Moreover, the tray or drawer may be removably secured to the warmer unit and warming cabinet compartments and be interchangeable with other drawers having different configurations to accommodate various items (e.g., instruments, blankets, etc.). In addition, the receptacles maybe interchangeable such that the tray or drawer may include bins or receptacles of various configurations to accommodate various quantities of items, varying item orientations (e.g., maintaining IV solution bags in an upright position) or items of different types or sizes. The tray or drawer may include any quantity or combination of fixed and/or interchangeable bins or receptacles.

The tray or drawer may include any quantity of monitoring assemblies to facilitate monitoring of receptacles and/or medical items. The monitoring assemblies maybe disposed at any suitable locations on the drawer within or external of the receptacles, maybe arranged in any suitable manner, may include any quantity of any type of sensors or other devices to measure any desired system, receptacle and/or item characteristics and may each correspond to or monitor any quantity of receptacles or items. The monitoring assemblies may be selectively disposed on the drawer to monitor each of the receptacles or any portion of the total quantity of receptacles. The temperature sensors of the monitoring assemblies maybe of any quantity, maybe disposed at any suitable locations on the drawer or assembly and maybe implemented by any type of temperature measuring device (e.g., RTD, NTC, infrared, thermocouple, etc.). The item sensor may be implemented by any type of sensor (e.g., a pressure, optical or magnetic switch, etc.). The item sensor housing may be of any shape or size, may be constructed of any suitable materials and may be mounted to the drawer at any suitable locations. The actuable assembly may be of any quantity, shape or size, may be disposed on the drawer or item sensor housing at any suitable locations and may include any type of device, contact and/or resilient member (e.g., spring, etc.) to provide a bias force and/or selective interfacing of the switch circuit (e.g., plunger, button, etc.). The contact member may be of any shape or size, may be constructed of any suitable materials and may include any quantity of temperature or other sensors disposed thereon at any suitable locations. The switch circuit may include any conventional or other circuitry generating a signal for the controller. The contact member may close the switch circuit or switch in any desired fashion (e.g., complete an electrical circuit, enable a voltage or current supply, etc.). The switch circuit may produce any desired signal to indicate the presence of a medical item to the controller (e.g., analog, digital, etc.). The tray or drawer may include any quantity of any type of connectors disposed at any suitable locations to connect the monitoring assemblies to the warmer unit and warming cabinet. Similarly, the warmer unit and warming cabinet may include any quantity of any type of connectors disposed at any suitable locations to be coupled with the tray or drawer connectors. Alternatively, the monitoring assemblies may communicate with the controller via any type of medium (e.g., wiring, cables, wireless, etc.). The connectors may be coupled via any conventional or other cable or wiring, or via direct engagement with each other.

The drawer mesh floor interior may be implemented by wire, rope or other material that enables air flow through the tray or drawer and can withstand the compartment temperature. The longitudinal and transverse dividers of the tray or drawer may be of any quantity, shape or size, may be implemented by any types of dividers that partition the drawer interior, and may be constructed of any suitable materials. These dividers may be attached to the drawer at any suitable locations via any conventional or other fastening techniques. The transverse and longitudinal dividers may include any quantity of wire members arranged in any fashion, whereby the wire members may include any quantity of wires arranged in any fashion. The divider wire members may be implemented by any wire, rope, cable, string or other line of any size or cross-sectional shape that can withstand the compartment temperature.

The tray or drawer floor may be implemented by any material or pattern enabling heated air to infiltrate the drawer and heat items contained therein, while the support wire members and peripheral wire members of those drawers may be implemented by any wire, rope, cable, string or other line of any size or cross-sectional shape that can withstand the compartment temperature. The support and peripheral wire members may be of any quantity, and may be disposed on the drawers in any fashion. The support bars, posts and other components (e.g., upper frame, floor, etc.) of the tray or drawer may be of any shape or size, may be constructed of any suitable materials and may be disposed on the drawers or arranged in any fashion. The tray or drawer may include any device that can configure the drawer interior into a large single receptacle or several individual receptacles. The drawer may include any configurations having a single receptacle of any shape or size, or any quantity of individual receptacles of any shape or size.

The control circuit may be disposed within the warmer unit at any suitable locations. The control circuit may be utilized and disposed at any locations within the warming cabinet and include additional components (e.g., controllers, relays, switches, etc.) to control corresponding warming cabinet compartments in substantially the same manner as the warmer unit compartment. The components of the control circuit may be implemented by any conventional components or other circuitry capable of performing the functions described herein. The thermocouple may be of any quantity, may be implemented by any conventional or other types of temperature sensors or other devices capable of measuring temperature, and may be disposed at any location within the warmer unit and warming cabinet compartments. The purge timer may be implemented by any conventional timers or other circuitry, and may be set to enable the fan for any desired time interval. The power receptacles may be implemented by any receptacles capable of interfacing a detachable power cord, or the circuit may include a power cord to receive power from a common wall outlet jack. The fan may be implemented by any conventional or other types of blowers, fans or other devices capable of directing air. The solid state relay may be implemented by any conventional or other types of switches, relays or other devices capable of controlling current/voltage to the heating coils.

The controllers of the warmer unit and warming cabinet may be implemented by any quantity of any conventional or other microprocessor, controller or circuitry, and may each control any quantity of compartments. The warmer unit and warming cabinet may include any quantity of any types of displays (e.g., LCD or LED) of any shape or size and disposed at any locations on or remote from the warmer unit and warming cabinet. The controls may be of any quantity, shape or size, maybe implemented by any suitable input devices (e.g., keypad, buttons, voice recognition, etc.) and may be disposed at any locations on the warmer unit and warming cabinet. The warmer unit and warming cabinet displays may each be associated with and provide information for any quantity of receptacles and may include any quantity of display fields including any desired information. Further, a display may selectively provide any information (e.g., residence time, insertion time, desired and actual temperatures or other information individually or in any combinations) for each receptacle or for any portion of the total quantity of receptacles. The display may be updated periodically, at any desired time interval and/or in response to the counters, controller input devices, controls and/or any desired conditions. A display field may correspond to and provide information for any quantity of receptacles, while the fields and receptacles may be associated by any type of identifier (e.g., alphanumeric identifier, symbols, icons, etc.). The display may alternatively provide any desired information in any format to a user. The warmer unit and warming cabinet may provide any visual (e.g., flash, bold, identify receptacle, etc.) and/or audio (e.g., beep or other sound, synthesized speech, etc.) alarms to notify a user of any desired conditions (e.g., item attaining or exceeding the set point or other temperature, time limit exceeded, etc.).

The controller may receive a compartment temperature and individual set point temperatures for each item. Thus, items associated with different set point temperatures may be heated within the same compartment, while the system notifies the user when each item has attained or exceeded the corresponding set point temperature via the visual and/or audio alarm. The counters may be implemented by any hardware (e.g., registers, circuitry, etc.) or software and may be incremented in response to any time interval (e.g., controller system clock, seconds or any fractions thereof, etc.) and/or conditions.

The controller may include any quantity of any types of displays (e.g., LCD, LED, etc.) of any shape or size and/or any quantity of any type of input devices (e.g., keypad, buttons, etc.) of any shape or size. The display and input devices may be disposed at any suitable locations on the controller and facilitate display and entry of any desired information.

The warmer unit and warming cabinet may be programmed to maintain compartments at any desired temperatures and may be utilized to heat various items for varying applications. Further, the warmer unit and warming cabinet may operate without recycling air by directing outside air through the compartments in substantially the same manner described above. The mixing of recycled and outside air maybe accomplished in any suitable or conventional manners. For example, valves may be utilized within the manifolds or ducts to control mixing, the speed of the fan directing recycled air back into a compartment may be controlled, or the rear panel slots may be covered or controlled to limit the amount of outside air entering the system. The warmer units of a multiple unit warming system may be operated either individually or in any combination or quantity to heat items contained within the units. Similarly, the compartments of the warming cabinet may be operated either individually or in any quantity or combination to heat items contained within the compartments. The warmer unit and warming cabinet may be operated via any suitable steps in any manner whereby the steps described above for operation of these systems may be selectively performed or performed in any desired sequence. The warmer unit and warming cabinet may be utilized without the tray or drawer by placing items within the warmer unit and warming cabinet compartments. Further, the warmer unit and warming cabinet may be utilized with various other medical apparatus to warm items prior to use within those apparatus (e.g., intravenous warming systems, thermal treatment machines, etc.).

From the foregoing description it will be appreciated that the invention makes available a novel warming system and method for heating various items utilized in surgical procedures wherein multiple individually controlled compartments of the system simultaneously maintain various items at different temperatures, while a corresponding compartment display indicates the temperature and residence times for the items heated within that compartment.

Having described preferred embodiments of a new and improved warming system and method for heating various items utilized in surgical procedures, it is believed that other modifications, variations and changes will be suggested to those skilled in the art in view of the teaching set forth herein. It is therefore to be understood that all such variations, modifications and changes are believed to fall within the scope of the present invention as defined by the appended claims.

What is claimed is:

1. A warming system for heating medical items to desired temperatures prior to using said medical items within medical procedures comprising:
    a warmer unit including:
        a housing;
        a compartment disposed within said housing to receive at least one medical item to be heated;
        a medical item support structure to receive and secure said at least one medical item within said compartment;
        a heater to heat said compartment and said at least one medical item disposed therein;
        a controller to control said heater to heat said compartment to a desired temperature and to determine at least one of a time of insertion and a residence time for at least one medical item disposed within said compartment; and
        a display to display at least one of said determined insertion time and residence time for at least one medical item disposed within said compartment.

2. The warming system of claim 1, wherein:
    said medical item support structure includes at least one receptacle each to selectively receive and secure a medical item within said compartment and at least one sensing assembly each associated with a corresponding receptacle to detect the presence of said medical item disposed within said corresponding receptacle; and
    said controller is coupled to each said sensing assembly and determines said residence time for each medical item disposed within said compartment based on information received from a corresponding sensing assembly.

3. The warming system of claim 2, wherein said medical item support structure includes a drawer configured for removable insertion into said compartment.

4. The warming system of claim 2, wherein said each sensing assembly includes a receptacle sensor to detect the presence of said medical item disposed within said corresponding receptacle.

5. The warming system of claim 4, wherein said each sensing assembly further includes a signal circuit to provide a signal to said controller indicating the presence of said medical item within said corresponding receptacle when said signal circuit is in a closed state;
    wherein said each receptacle sensor includes a circuit member to close a corresponding signal circuit and provide said signal when a medical item is received within said corresponding receptacle and to open said corresponding signal circuit when said medical item is absent from said corresponding receptacle.

6. The warming system of claim 5, wherein said controller includes at least one counter each associated with a corresponding receptacle to maintain said residence time for said medical item received within said corresponding receptacle in response to said signal provided by said corresponding signal circuit.

7. The warming system of claim 5, wherein said contact member of said each receptacle sensor includes at least one temperature sensor to measure a temperature of said medical item disposed within said corresponding receptacle.

8. The warming system of claim 5, wherein said each sensing assembly is disposed proximate a floor portion of a corresponding receptacle and said each contact member interfaces a corresponding signal circuit in response to forces applied by a medical item to that contact member upon insertion into the receptacle.

9. The warming system of claim 4, wherein said each sensing assembly further includes a temperature sensor to measure a temperature of said medical item disposed within said corresponding receptacle.

10. The warming system of claim 9 further including an input device to facilitate entry of desired temperatures for said compartment and each medical item contained therein.

11. The warming system of claim 10 further including at least one alarm to indicate occurrence of a particular condition to a user.

12. The warming system of claim 11, wherein said alarm includes at least one of a visual and audio indicator and said condition includes a measured temperature of a medical item disposed within a receptacle exceeding a corresponding desired temperature.

13. The warming system of claim 2, wherein said controller determines said insertion time for each medical item disposed within said compartment indicating when that medical item is disposed within a corresponding receptacle in response to said corresponding sensing assembly detecting the presence of that medical item within said corresponding receptacle.

14. The warming system of claim 10, wherein said display further displays for at least one medical item disposed within said compartment at least one of said corresponding desired temperature and said measured temperature of said medical item.

15. The warming system of claim 14, wherein said display includes at least one display field each associated with a corresponding receptacle to display information associated with that receptacle.

16. The warming system of claim 1, wherein said heater includes:
   a heating element; and
   a fan to direct air across said heating element to produce heated air and to direct said heated air into said compartment to heat said compartment and said at least one medical item contained therein.

17. The warming system of claim 1, further comprising:
   a plurality of said warmer units each individually controllable to heat said medical items to said desired temperatures, wherein said each warmer unit maintains a corresponding desired temperature and said warming system simultaneously heats said medical items contained within said warmer units to respective desired temperatures entered for said warmer units.

18. The warming system of claim 1, wherein said warmer unit further includes:
   a plurality of said compartments for heating said medical items to said desired temperatures, wherein each said compartment maintains a corresponding desired temperature;
   a plurality of said heaters each heating a corresponding compartment;
   a plurality of said medical item support structures each disposed within a corresponding compartment for receiving and securing at least one medical item within that compartment;
   a plurality of said controllers each to control said corresponding heater to heat said corresponding compartment to the desired temperature for that compartment and to determine at least one of said insertion time and residence time for at least one medical item disposed within that compartment; and
   a plurality of displays each associated with a corresponding compartment to display at least one of said determined insertion time and residence time for at least one medical item disposed within said corresponding compartment;
   wherein said warming unit simultaneously heats medical items contained within said compartments to respective desired temperatures entered for said compartments.

19. A carrier for use with a warming system for heating medical items to desired temperatures prior to using said medical items within medical procedures, said carrier comprising:
   a frame including an interior partitioned into a plurality of receptacles each to receive and retain a medical item therein; and
   a plurality of sensing assemblies each associated with and disposed proximate a corresponding receptacle to monitor that receptacle and said medical item contained therein;
   wherein said carrier is configured for removable insertion within a compartment of said warming system to facilitate heating of said medical items disposed within said receptacles.

20. The carrier of claim 19, wherein said each sensing assembly includes a receptacle sensor to detect the presence of said medical item disposed within said corresponding receptacle.

21. The carrier of claim 20, wherein said each sensing assembly further includes a signal circuit to provide a signal to a warming system controller indicating the presence of said medical item within said corresponding receptacle when said signal circuit is in a closed state;
   wherein said each receptacle sensor includes a circuit member to close a corresponding signal circuit and provide said signal when a medical item is received within said corresponding receptacle and to open said corresponding signal circuit when said medical item is absent from said corresponding receptacle.

22. The carrier of claim 21, wherein said contact member of said each receptacle sensor includes at least one temperature sensor to measure a temperature of said medical item disposed within said corresponding receptacle.

23. The carrier of claim 21, wherein said each sensing assembly is disposed proximate a floor portion of a corresponding receptacle and said each contact member interfaces a corresponding signal circuit in response to forces applied by a medical item to that contact member upon insertion into the receptacle.

24. The carrier of claim 20, wherein said each sensing assembly further includes a temperature sensor to measure a temperature of said medical item disposed within said corresponding receptacle.

25. In a warming system including a warmer unit including a compartment, a medical item support structure to receive and secure at least one medical item within said compartment, a heater to heat said compartment, a controller to control said heater and a display, a method of heating medical items to desired temperatures prior to using said medical items within medical procedures comprising the steps of:
   (a) receiving at least one medical item to be heated within said compartment;
   (b) heating said compartment and said at least one medical item disposed therein via said heater;
   (c) controlling said heater to heat said compartment to a desired temperature and determining at least one of a time of insertion and a residence time for at least one medical item disposed within said compartment; and
   (d) displaying at least one of said determined insertion time and residence time for at least one medical item disposed within said compartment.

26. The method of claim 25, wherein said medical item support structure includes at least one receptacle each to selectively receive and secure a medical item within said compartment and at least one sensing assembly each associated with a corresponding receptacle, and step (a) further includes:
   (a.1) detecting, via an associated sensing assembly, the presence of said medical item disposed within said corresponding receptacle; and
   step (c) further includes:
   (c.1) determining said residence time for each medical item disposed within said compartment based on information received from a corresponding sensing assembly.

27. The method of claim 26, wherein said each sensing assembly includes a receptacle sensor, and step (a.1) further includes:
   (a.1.1) detecting the presence of said medical item disposed within said corresponding receptacle via an associated receptacle sensor.

28. The method of claim 27, wherein said each sensing assembly further includes a signal circuit to provide a signal to said controller indicating the presence of said medical item within said corresponding receptacle when said signal circuit is in a closed state, and step (a.1.1) further includes:
   (a.1.1.1) closing a corresponding signal circuit, via a contact member of an associated receptacle sensor, to provide said signal when a medical item is received within said corresponding receptacle and opening said corresponding signal circuit when said medical item is absent from said corresponding receptacle.

29. The method of claim 28, wherein said controller includes at least one counter each associated with a corresponding receptacle, and step (c.1) further includes:
   (c.1.1) maintaining said residence time for said medical item received within said corresponding receptacle via an associated counter in response to said signal provided by said corresponding signal circuit.

30. The method of claim 28, wherein said contact member of said each receptacle sensor includes at least one temperature sensor, and step (b) further includes:
   (b.1) measuring a temperature of said medical item disposed within said corresponding receptacle via an associated contact member temperature sensor.

31. The method of claim 28, wherein said each sensing assembly is disposed proximate a floor portion of a corresponding receptacle, and step (a.1.1.1) further includes:
   (a.1.1.1.1) interfacing a contact member to a corresponding signal circuit in response to forces applied by a medical item to that contact member upon insertion into the receptacle.

32. The method of claim 27, wherein said each sensing assembly further includes a temperature sensor, and step (b) further includes:
   (b.1) measuring a temperature of said medical item disposed within said corresponding receptacle via an associated temperature sensor.

33. The method of claim 32, wherein said warming system further includes an input device, and step (a.1.1) further includes:
   (a.1.1.1) facilitating entry of desired temperatures for said compartment and each medical item contained therein.

34. The method of claim 33, wherein step (b) further includes:
   (b.1) indicating occurrence of a particular condition to a user via at least one alarm.

35. The method of claim 34, wherein step (b.1) further includes:
   (b.1.1) indicating occurrence of a measured temperature of a medical item disposed within a receptacle exceeding a corresponding desired temperature via said alarm, wherein said alarm includes at least one of a visual and audio indicator.

36. The method of claim 26, wherein step (c.1) further includes:
   (c.1.1) determining said insertion time for each medical item disposed within said compartment indicating when that medical item is disposed within a corresponding receptacle in response to said corresponding sensing assembly detecting the presence of that medical item within said corresponding receptacle.

37. The method of claim 33, wherein step (d) further includes:
   (d.1) displaying for each medical item disposed within said compartment at least one of said corresponding desired temperature and said measured temperature of said medical item.

38. The method of claim 37, wherein said display includes at least one display field each associated with a corresponding receptacle, and step (d.1) further includes:
   (d.1.1) displaying information associated with a receptacle within a corresponding display field.

39. The method of claim 25, wherein said heater includes a heating element and a fan, and step (b) further includes:
   (b.1) directing air across said heating element to produce heated air and directing said heated air into said compartment to heat said compartment and said at least one medical item contained therein.

40. The method of claim 25, wherein said warming system further includes a plurality of said warmer units each individually controllable to heat said medical items to said desired temperatures, wherein step (a) further includes:
   (a.1) receiving at least one medical item to be heated within compartments of at least two warmer units;
   step (b) further includes:
      (b.1) heating said compartments of said at least two warmer units and said medical items disposed therein via corresponding heaters;
   step (c) further includes:
      (c.1) controlling said heaters of said at least two warmer units to heat corresponding compartments to respective desired temperatures associated with those compartments and determining at least one of said insertion time and residence time for at least one medical item within each of those compartments; and
   step (d) further includes:
      (d.1) displaying at least one of said insertion time and residence time for at least one medical item within each of said compartments of said at least two warmer units;
   wherein said each warmer unit maintains a corresponding desired temperature and said warming system simultaneously heats said medical items contained within said warmer units to respective desired temperatures entered for said warmer units.

41. The method of claim 25, wherein said warmer unit further includes a plurality of said compartments for heating said medical items to said desired temperatures, wherein each said compartment maintains a corresponding desired temperature, a plurality of said heaters each heating a corresponding compartment, a plurality of said medical item support structures each disposed within a corresponding compartment for receiving and securing at least one medical item within that compartment, a plurality of said controllers each to control said corresponding heater to heat said corresponding compartment to the desired temperature for that compartment and a plurality of displays each associated with a corresponding compartment, and step (a) further includes:
   (a.1) receiving at least one medical item to be heated within at least two compartments;
   step (b) further includes:
      (b.1) heating said at least two compartments and said medical items disposed therein via corresponding heaters;
   step (c) further includes:
      (c.1) controlling said heaters of said at least two compartments to heat those compartments to respective desired temperatures associated with those compartments and determining at least one of said insertion time and residence time for at least one medical item within each of said at least two compartments; and
   step (d) further includes:
      (d.1) displaying at least one of said determined insertion time and residence time for at least one medical item within each of said at least two compartments;

wherein said warming unit simultaneously heats medical items contained within said at least two compartments to respective desired temperatures entered for those compartments.

42. A warming system for heating medical items to desired temperatures prior to using said medical items within medical procedures comprising:

a housing;

a compartment disposed within said housing to receive medical items to be heated;

a medical item support structure configured for removable insertion into said compartment and including a plurality of receptacles each to selectively receive and secure a medical item within said compartment and a plurality of sensing assemblies each associated with a corresponding receptacle to monitor that receptacle and said medical item disposed therein;

a heater to heat said compartment and said medical items disposed therein;

a controller to control said heater to heat said compartment to a desired temperature; and a display to display information associated with each medical item disposed within said compartment, wherein said displayed information includes information from said sensing assemblies.

43. The warming system of claim 42, wherein said each sensing assembly includes a receptacle sensor to detect the presence of said medical item disposed within said corresponding receptacle.

44. The warming system of claim 43, wherein said each sensing assembly further includes a temperature sensor to measure a temperature of said medical item disposed within said corresponding receptacle.

45. The warming system of claim 44 further including an input device to facilitate entry of desired temperatures for said compartment and each medical item contained therein.

46. The warming system of claim 45, wherein said controller is coupled to each said sensing assembly and determines a residence time for each medical item disposed within said compartment based on information received from a corresponding sensing assembly.

47. The warming system of claim 46, wherein said controller further determines an insertion time for each medical item disposed within said compartment indicating when that medical item is disposed within a corresponding receptacle in response to information received from said corresponding sensing assembly.

48. The warming system of claim 47, wherein said display displays for each medical item disposed within said compartment at least one of said residence time, said insertion time, said corresponding desired temperature and said measured temperature of said medical item.

49. In a warming system including a warmer unit including a compartment, a medical item support structure including a plurality of receptacles each to selectively receive and secure a medical item within said compartment and a plurality of sensing assemblies each associated with a corresponding receptacle, a heater to heat said compartment, a controller to control said heater and a display, a method of heating medical items to desired temperatures prior to using said medical items within medical procedures comprising the steps of:

(a) receiving medical items to be heated within said receptacles;

(b) heating said compartment and said medical items disposed therein via said heater;

(c) controlling said heater to heat said compartment to a desired temperature;

(d) monitoring the receptacles and medical items disposed therein via the sensing assemblies; and (e) displaying information associated with each medical item disposed within said compartment, wherein said displayed information includes information from said sensing assemblies.

50. The method of claim 49, wherein said each sensing assembly includes a receptacle sensor, and step (d) further includes:

(d.1) detecting the presence of said medical item disposed within said corresponding receptacle via an associated receptacle sensor.

51. The method of claim 50, wherein said each sensing assembly further includes a temperature sensor, and step (d) further includes:

(d.1) measuring a temperature of said medical item disposed within said corresponding receptacle via an associated temperature sensor.

52. The method of claim 51, wherein said warming system further includes an input device, and step (a) further includes:

(a.1) facilitating entry of desired temperatures for said compartment and each medical item contained therein.

53. The method of claim 52, wherein step (e) further includes:

(e.1) determining said residence time for each medical item disposed within said compartment based on information received from a corresponding sensing assembly.

54. The method of claim 53, wherein step (e) further includes:

(e.2) determining an insertion time for each medical item disposed within said compartment indicating when that medical item is disposed within a corresponding receptacle in response to information received from said corresponding sensing assembly.

55. The method of claim 54, wherein step (e) further includes:

(e.3) displaying for each medical item disposed within said compartment at least one of said residence time, said insertion time, said corresponding desired temperature and said measured temperature of said medical item.

56. A warming system for heating medical items to desired temperatures prior to using said medical items within medical procedures comprising:

a housing;

a compartment disposed within said housing to receive at least one medical item to be heated;

medical item support means for receiving and securing said at least one medical item within said compartment;

heating means for heating said compartment and said at least one medical item disposed therein;

control means for controlling said heating means to heat said compartment to a desired temperature and for determining at least one of a time of insertion and a residence time for at least one medical item disposed within said compartment; and display means for displaying at least one of said determined insertion time and residence time for at least one medical item disposed within said compartment.

57. The warming system of claim 56, wherein said medical item support means includes at least one receptacle each to selectively receive and secure a medical item within said compartment and at least one sensing means each associated with a corresponding receptacle for monitoring that receptacle and including receptacle sensing means for detecting the presence of said medical item disposed within said corresponding receptacle, and wherein said control means determines said residence time for each medical item disposed within said compartment based on information received from a corresponding sensing means.

58. The warming system of claim 57, wherein said each sensing means further includes temperature sensing means to measure a temperature of said medical item disposed within said corresponding receptacle.

59. The warming system of claim 58, wherein said control means determines said insertion time for each medical item disposed within said compartment indicating when that medical item is disposed within a corresponding receptacle in response to said corresponding sensing means detecting the presence of that medical item within said corresponding receptacle.

60. The warming system of claim 59, wherein said display means further displays for each medical item disposed within said compartment at least one of said desired temperature and said measured temperature of said medical item.

61. A carrier for use with a warming system for heating medical items to desired temperatures prior to using said medical items within medical procedures, said carrier comprising:
- a frame including an interior partitioned into a plurality of receptacles each to receive and retain a medical item therein; and
- a plurality of sensing means each associated with and disposed proximate a corresponding receptacle for monitoring that receptacle and said medical item contained therein;
- wherein said carrier is configured for removable insertion within a compartment of said warming system to facilitate heating of said medical items disposed within said receptacles.

62. The carrier of claim 61, wherein said each sensing means includes receptacle sensing means for detecting the presence of said medical item disposed within said corresponding receptacle.

63. The carrier of claim 62, wherein said each sensing means further includes temperature sensing means for measuring a temperature of said medical item disposed within said corresponding receptacle.

64. A warming system for heating medical items to desired temperatures prior to using said medical items within medical procedures comprising:
- a housing;
- a compartment disposed within said housing to receive medical items to be heated;
- medical item support means configured for removable insertion into said compartment and including a plurality of receptacles each to selectively receive and secure a medical item within said compartment and a plurality of sensing means each associated with a corresponding receptacle for monitoring that receptacle and said medical item disposed therein;
- heating means for heating said compartment and said medical items disposed therein;
- control means for controlling said heating means to heat said compartment to a desired temperature; and
- display means for displaying information associated with each medical item disposed within said compartment, wherein said displayed information includes information from said sensing means.

65. The warming system of claim 64, wherein said each sensing means includes receptacle sensing means for detecting the presence of said medical item disposed within said corresponding receptacle.

66. The warming system of claim 65, wherein said each sensing means further includes temperature sensing means for measuring a temperature of said medical item disposed within said corresponding receptacle.

67. The warming system of claim 66, wherein said control means is coupled to each said sensing means and determines a residence time for each medical item disposed within said compartment based on information received from a corresponding sensing means.

68. The warming system of claim 67, wherein said control means further determines an insertion time for each medical item disposed within said compartment indicating when that medical item is disposed within a corresponding receptacle in response to information received from said corresponding sensing means.

69. The warming system of claim 68, wherein said display means displays for each medical item disposed within said compartment at least one of said residence time, said insertion time, said desired temperature and said measured temperature of said medical item.

* * * * *